(12) United States Patent
Helf et al.

(10) Patent No.: US 8,381,951 B2
(45) Date of Patent: Feb. 26, 2013

(54) OVERCAP FOR A SPRAY DEVICE

(75) Inventors: Thomas A. Helf, New Berlin, WI (US); Edward L. Paas, Los Altos, CA (US)

(73) Assignee: S.C. Johnson & Son, Inc., Racine, WI (US)

( * ) Notice: Subject to any disclaimer, the term of this patent is extended or adjusted under 35 U.S.C. 154(b) by 1211 days.

(21) Appl. No.: 11/893,456

(22) Filed: Aug. 16, 2007

(65) Prior Publication Data

US 2009/0045218 A1 Feb. 19, 2009

(51) Int. Cl.
*B67D 7/06* (2010.01)

(52) U.S. Cl. ............. 222/504; 222/402.21; 222/402.13; 239/102.2

(58) Field of Classification Search ............. 222/402.13, 222/649, 52, 504, 402.21–402.23, 181.1–181.3, 222/63, 196, 638–639, 645–648; 239/102.1, 239/102.2, 144, 142, 237; 251/349–354
See application file for complete search history.

(56) References Cited

U.S. PATENT DOCUMENTS

| | | | |
|---|---|---|---|
| 2,608,319 A | 8/1952 | Petry | |
| 2,613,108 A | 10/1952 | Kraus | |
| 2,928,573 A | 3/1960 | Edelstein | |
| 3,018,056 A | 1/1962 | Montgomery | |
| 3,115,277 A | 12/1963 | Montague, Jr. | |
| 3,127,060 A | 3/1964 | Vosbikian et al. | |
| 3,165,238 A | 1/1965 | Wiley | |
| 3,180,532 A | 4/1965 | Michel | |
| 3,185,356 A | 5/1965 | Venus, Jr. | |
| 3,198,394 A * | 8/1965 | Lefer | 222/135 |
| 3,199,732 A | 8/1965 | Strachan | |
| 3,228,609 A | 1/1966 | Edelstein et al. | |
| 3,240,389 A * | 3/1966 | Genua | 222/645 |
| 3,269,602 A | 8/1966 | Weber, III | |
| 3,273,610 A | 9/1966 | Frost | |
| 3,289,886 A | 12/1966 | Goldsholl et al. | |
| 3,305,134 A | 2/1967 | Carmichael et al. | |
| 3,326,418 A | 6/1967 | Kropp | |
| 3,329,314 A | 7/1967 | Kolodziej | |
| 3,368,717 A | 2/1968 | Weber, III | |
| 3,398,864 A | 8/1968 | Kolodziej | |
| 3,411,670 A | 11/1968 | Mangel | |
| 3,419,189 A | 12/1968 | Iketani | |
| 3,455,485 A | 7/1969 | Crownover | |
| 3,477,613 A | 11/1969 | Mangel | |
| 3,497,108 A | 2/1970 | Mason | |
| 3,497,110 A | 2/1970 | Bombero et al. | |
| 3,542,248 A | 11/1970 | Mangel | |

(Continued)

FOREIGN PATENT DOCUMENTS

| | | |
|---|---|---|
| EP | 656230 | 6/1995 |
| EP | 0676133 A1 | 10/1995 |

(Continued)

OTHER PUBLICATIONS

English Translation of JP 2003-246380.*

(Continued)

*Primary Examiner* — Kevin P Shaver
*Assistant Examiner* — Robert Nichols, II

(57) ABSTRACT

A dispensing system includes a tilt-activated valve stem operably connected to a valve on a container and a vibe motor in communication with the valve stem. The vibe motor is adapted to impart radial motion to the valve stem upon activation.

12 Claims, 18 Drawing Sheets

U.S. PATENT DOCUMENTS

| | | |
|---|---|---|
| 3,543,122 A | 11/1970 | Klebanoff et al. |
| 3,584,766 A | 6/1971 | Hart et al. |
| 3,589,562 A | 6/1971 | Buck |
| 3,589,563 A | 6/1971 | Carragan et al. |
| 3,591,058 A | 7/1971 | Johnston |
| 3,617,214 A | 11/1971 | Dolac |
| 3,620,023 A | 11/1971 | Schmid |
| 3,627,176 A | 12/1971 | Sailors |
| 3,632,020 A | 1/1972 | Nixon, Jr. et al. |
| 3,643,836 A | 2/1972 | Hunt |
| 3,658,209 A | 4/1972 | Freeman et al. |
| 3,664,548 A | 5/1972 | Broderick |
| 3,666,144 A | 5/1972 | Winder |
| 3,677,441 A | 7/1972 | Nixon, Jr. et al. |
| 3,690,519 A | 9/1972 | Wassilieff |
| 3,722,749 A | 3/1973 | Ishida |
| 3,726,437 A | 4/1973 | Siegel |
| 3,732,509 A | 5/1973 | Florant et al. |
| 3,739,944 A | 6/1973 | Rogerson |
| 3,756,465 A | 9/1973 | Meshberg |
| 3,794,216 A | 2/1974 | Buck |
| 3,817,429 A | 6/1974 | Smrt |
| 3,870,274 A | 3/1975 | Broe |
| 3,885,712 A | 5/1975 | Libit |
| 3,929,259 A | 12/1975 | Fegley et al. |
| 3,952,916 A | 4/1976 | Phillips |
| 3,968,905 A | 7/1976 | Pelton |
| 3,974,941 A | 8/1976 | Mettler |
| 3,980,205 A | 9/1976 | Smart |
| RE29,117 E * | 1/1977 | Sahajian et al. ............... 222/649 |
| 4,004,550 A | 1/1977 | White et al. |
| 4,006,844 A | 2/1977 | Corris |
| 4,063,664 A | 12/1977 | Meetze, Jr. |
| 4,064,573 A | 12/1977 | Calderone |
| 4,068,575 A | 1/1978 | Difley et al. |
| 4,068,780 A | 1/1978 | Fegley |
| 4,077,542 A | 3/1978 | Petterson |
| 4,096,974 A | 6/1978 | Haber et al. |
| 4,184,612 A | 1/1980 | Freyre |
| 4,235,373 A | 11/1980 | Clark |
| 4,238,055 A | 12/1980 | Staar |
| 4,275,821 A | 6/1981 | Lanno et al. |
| 4,396,152 A | 8/1983 | Abplanalp |
| 4,415,797 A | 11/1983 | Choustoulakis |
| 4,483,466 A | 11/1984 | Gutierrez |
| 4,544,086 A | 10/1985 | Hill et al. |
| 4,658,985 A | 4/1987 | Madsen et al. |
| 4,877,989 A | 10/1989 | Drews et al. |
| 4,967,935 A | 11/1990 | Celest |
| 4,989,755 A | 2/1991 | Shiau |
| 4,993,570 A | 2/1991 | Julian et al. |
| 5,012,961 A | 5/1991 | Madsen et al. |
| 5,014,881 A | 5/1991 | Andris |
| 5,018,963 A | 5/1991 | Diederich |
| 5,025,962 A | 6/1991 | Renfro |
| 5,029,729 A | 7/1991 | Madsen et al. |
| 5,038,972 A | 8/1991 | Muderlak et al. |
| 5,055,822 A | 10/1991 | Campbell et al. |
| 5,098,291 A | 3/1992 | Curtis et al. |
| 5,134,961 A | 8/1992 | Giles et al. |
| 5,154,323 A | 10/1992 | Query et al. |
| 5,198,157 A | 3/1993 | Bechet |
| 5,221,025 A | 6/1993 | Privas |
| 5,249,718 A | 10/1993 | Muderlak |
| 5,297,988 A | 3/1994 | Nishino et al. |
| 5,337,926 A | 8/1994 | Drobish et al. |
| 5,337,929 A | 8/1994 | van der Heijden |
| 5,342,584 A | 8/1994 | Fritz et al. |
| 5,353,744 A | 10/1994 | Custer |
| 5,364,028 A | 11/1994 | Wozniak |
| 5,383,580 A | 1/1995 | Winder |
| RE34,847 E | 2/1995 | Muderlak et al. |
| 5,392,768 A | 2/1995 | Johansson et al. |
| 5,397,028 A | 3/1995 | Jesadanont |
| 5,445,324 A | 8/1995 | Berry et al. |
| 5,447,273 A | 9/1995 | Wozniak |
| 5,447,277 A | 9/1995 | Schlüter et al. |
| 5,449,117 A | 9/1995 | Muderlak et al. |
| 5,489,047 A | 2/1996 | Winder |
| 5,503,303 A | 4/1996 | LaWare et al. |
| 5,522,722 A | 6/1996 | Diederich |
| 5,531,344 A | 7/1996 | Winner |
| 5,540,359 A | 7/1996 | Gobbel |
| 5,542,605 A | 8/1996 | Campau |
| 5,549,228 A | 8/1996 | Brown |
| 5,588,565 A | 12/1996 | Miller |
| 5,601,235 A | 2/1997 | Booker et al. |
| 5,622,162 A | 4/1997 | Johansson et al. |
| 5,673,825 A | 10/1997 | Chen |
| 5,676,283 A | 10/1997 | Wang |
| 5,685,456 A | 11/1997 | Goldstein |
| 5,695,091 A | 12/1997 | Winings et al. |
| 5,702,036 A | 12/1997 | Ferrara, Jr. |
| 5,743,251 A | 4/1998 | Howell et al. |
| 5,772,074 A | 6/1998 | Dial et al. |
| 5,787,947 A | 8/1998 | Hertsgaard |
| 5,791,524 A | 8/1998 | Demarest |
| 5,810,265 A | 9/1998 | Cornelius et al. |
| 5,823,390 A | 10/1998 | Muderlak et al. |
| 5,842,602 A | 12/1998 | Pierpoint |
| 5,853,129 A | 12/1998 | Spitz |
| 5,884,808 A | 3/1999 | Muderlak et al. |
| 5,908,140 A | 6/1999 | Muderlak et al. |
| 5,922,247 A | 7/1999 | Shoham et al. |
| 5,924,597 A | 7/1999 | Lynn |
| 5,938,076 A | 8/1999 | Ganzeboom |
| 5,964,403 A | 10/1999 | Miller et al. |
| 6,000,658 A | 12/1999 | McCall, Jr. |
| 6,006,957 A | 12/1999 | Kunesh |
| 6,036,108 A | 3/2000 | Chen |
| 6,039,212 A | 3/2000 | Singh |
| 6,089,410 A | 7/2000 | Ponton |
| 6,145,712 A | 11/2000 | Benoist |
| 6,182,904 B1 | 2/2001 | Ulczynski et al. |
| 6,216,925 B1 | 4/2001 | Garon |
| 6,220,293 B1 | 4/2001 | Rashidi |
| 6,237,812 B1 | 5/2001 | Fukada |
| 6,249,717 B1 | 6/2001 | Nicholson et al. |
| 6,254,065 B1 | 7/2001 | Ehrensperger et al. |
| 6,260,739 B1 | 7/2001 | Hsiao |
| 6,267,297 B1 | 7/2001 | Contadini et al. |
| 6,276,574 B1 | 8/2001 | Smrt |
| 6,293,442 B1 | 9/2001 | Mollayan |
| 6,293,474 B1 | 9/2001 | Helf et al. |
| 6,321,742 B1 | 11/2001 | Schmidt et al. |
| 6,338,424 B2 | 1/2002 | Nakamura et al. |
| 6,343,714 B1 | 2/2002 | Tichenor |
| 6,394,310 B1 | 5/2002 | Muderlak et al. |
| 6,409,093 B2 | 6/2002 | Ulczynski et al. |
| 6,419,122 B1 | 7/2002 | Chown |
| 6,454,185 B2 | 9/2002 | Fuchs |
| 6,478,199 B1 | 11/2002 | Shanklin et al. |
| 6,510,561 B1 | 1/2003 | Hammond et al. |
| 6,517,009 B2 | 2/2003 | Yahav |
| 6,533,141 B1 | 3/2003 | Petterson et al. |
| 6,540,155 B1 | 4/2003 | Yahav |
| 6,554,203 B2 | 4/2003 | Hess et al. |
| 6,567,613 B2 | 5/2003 | Rymer |
| 6,588,627 B2 | 7/2003 | Petterson et al. |
| 6,612,464 B2 | 9/2003 | Petterson et al. |
| 6,616,363 B1 | 9/2003 | Guillaume et al. |
| 6,619,562 B2 | 9/2003 | Hamaguchi et al. |
| 6,644,507 B2 | 11/2003 | Borut et al. |
| 6,645,307 B2 | 11/2003 | Fox et al. |
| 6,669,105 B2 | 12/2003 | Bryan et al. |
| 6,688,492 B2 | 2/2004 | Jaworski et al. |
| 6,694,536 B1 | 2/2004 | Haygreen |
| 6,701,663 B1 | 3/2004 | Hughes et al. |
| 6,708,849 B1 | 3/2004 | Carter et al. |
| D488,548 S | 4/2004 | Lablaine |
| 6,722,529 B2 | 4/2004 | Ceppaluni et al. |
| 6,739,479 B2 | 5/2004 | Contadini et al. |
| 6,769,580 B2 | 8/2004 | Muderlak et al. |
| 6,776,968 B2 | 8/2004 | Edwards et al. |
| 6,785,911 B1 | 9/2004 | Percher |
| 6,790,408 B2 | 9/2004 | Whitby et al. |
| 6,832,701 B2 | 12/2004 | Schiller |

| | | |
|---|---|---|
| 6,837,396 B2 | 1/2005 | Jaworski et al. |
| 6,843,465 B1 | 1/2005 | Scott |
| 6,877,636 B2 | 4/2005 | Speckhart et al. |
| 6,918,512 B2 | 7/2005 | Kondoh |
| 6,926,002 B2 | 8/2005 | Scarrott et al. |
| 6,926,172 B2 | 8/2005 | Jaworski et al. |
| 6,926,211 B2 | 8/2005 | Bryan et al. |
| 6,938,796 B2 | 9/2005 | Blacker et al. |
| 6,971,560 B1 | 12/2005 | Healy et al. |
| 6,974,091 B2 | 12/2005 | McLisky |
| 6,978,947 B2 | 12/2005 | Jin |
| D513,433 S | 1/2006 | Lemaire |
| 6,997,349 B2 | 2/2006 | Blacker et al. |
| 7,000,853 B2 | 2/2006 | Fugere |
| 7,028,917 B2 | 4/2006 | Buthier |
| 7,032,782 B1 | 4/2006 | Ciavarella et al. |
| D520,623 S | 5/2006 | Lablaine |
| 7,044,337 B1 | 5/2006 | Kou |
| 7,051,455 B2 | 5/2006 | Bedford |
| D525,693 S | 7/2006 | Butler et al. |
| D527,472 S | 8/2006 | Barraclough et al. |
| D532,891 S | 11/2006 | Buthier et al. |
| 7,141,125 B2 | 11/2006 | McKechnie et al. |
| D536,059 S | 1/2007 | King et al. |
| D536,082 S | 1/2007 | Pugh |
| 7,168,631 B2 | 1/2007 | Jones |
| 7,182,227 B2 | 2/2007 | Poile et al. |
| D537,914 S | 3/2007 | King et al. |
| D538,915 S | 3/2007 | Anderson et al. |
| 7,192,610 B2 | 3/2007 | Hughes et al. |
| 7,195,139 B2 | 3/2007 | Jaworski et al. |
| D540,931 S | 4/2007 | Luo |
| 7,223,361 B2 | 5/2007 | Kvietok et al. |
| 7,249,720 B2 | 7/2007 | Mathiez |
| 2002/0020756 A1 | 2/2002 | Yahav |
| 2003/0089734 A1 | 5/2003 | Eberhardt et al. |
| 2003/0132254 A1 | 7/2003 | Giangreco |
| 2004/0011885 A1 | 1/2004 | McLisky |
| 2004/0028551 A1 | 2/2004 | Kvietok et al. |
| 2004/0033171 A1 | 2/2004 | Kvietok et al. |
| 2004/0035949 A1 | 2/2004 | Elkins et al. |
| 2004/0074935 A1 | 4/2004 | Chon |
| 2004/0155056 A1 | 8/2004 | Yahav |
| 2004/0219863 A1 | 11/2004 | Willacy |
| 2005/0004714 A1 | 1/2005 | Chen |
| 2005/0023287 A1 | 2/2005 | Speckhart et al. |
| 2005/0139624 A1 | 6/2005 | Hooks et al. |
| 2005/0155985 A1 | 7/2005 | Meyer |
| 2005/0201944 A1 | 9/2005 | Kvietok et al. |
| 2005/0224596 A1 | 10/2005 | Panopoulos |
| 2005/0247735 A1* | 11/2005 | Muderlak et al. ............. 222/190 |
| 2005/0252930 A1 | 11/2005 | Contadini et al. |
| 2005/0279853 A1 | 12/2005 | McLeisch et al. |
| 2006/0011737 A1 | 1/2006 | Amenos et al. |
| 2006/0037532 A1 | 2/2006 | Eidson |
| 2006/0060615 A1 | 3/2006 | McLisky |
| 2006/0076366 A1 | 4/2006 | Furner et al. |
| 2006/0081661 A1 | 4/2006 | Lasserre et al. |
| 2006/0083632 A1 | 4/2006 | Hammond et al. |
| 2006/0118658 A1 | 6/2006 | Corkhill et al. |
| 2006/0124477 A1 | 6/2006 | Cornelius et al. |
| 2006/0140901 A1 | 6/2006 | McKechnie |
| 2006/0151546 A1 | 7/2006 | McLisky |
| 2006/0153733 A1 | 7/2006 | Sassoon |
| 2006/0175341 A1 | 8/2006 | Rodrian |
| 2006/0175357 A1 | 8/2006 | Hammond |
| 2006/0175426 A1 | 8/2006 | Schramm et al. |
| 2006/0191955 A1 | 8/2006 | McLisky |
| 2006/0196576 A1 | 9/2006 | Fleming et al. |
| 2006/0210421 A1 | 9/2006 | Hammond et al. |
| 2006/0219740 A1 | 10/2006 | Bayer |
| 2006/0229232 A1 | 10/2006 | Contadini et al. |
| 2006/0243762 A1 | 11/2006 | Sassoon |
| 2006/0255176 A1* | 11/2006 | Yeiser ..................... 239/263.1 |
| 2007/0012718 A1 | 1/2007 | Schramm et al. |
| 2007/0062980 A1 | 3/2007 | Bates et al. |
| 2007/0071933 A1 | 3/2007 | Gavelli et al. |
| 2007/0087953 A1 | 4/2007 | McKechnie et al. |
| 2007/0093558 A1 | 4/2007 | Harper et al. |
| 2007/0138326 A1 | 6/2007 | Hu |
| 2007/0158359 A1 | 7/2007 | Rodrian |
| 2009/0108094 A1* | 4/2009 | Ivri .............................. 239/101 |

FOREIGN PATENT DOCUMENTS

| | | |
|---|---|---|
| EP | 0826607 | 3/1998 |
| EP | 0826608 | 3/1998 |
| EP | 1184083 A1 | 3/2002 |
| EP | 1214949 A2 | 6/2002 |
| EP | 1316514 | 6/2003 |
| EP | 1382399 A1 | 1/2004 |
| EP | 1430958 A2 | 6/2004 |
| EP | 1522506 A1 | 4/2005 |
| EP | 1328757 | 5/2006 |
| EP | 1695720 A1 | 8/2006 |
| EP | 1702512 | 9/2006 |
| EP | 1702513 | 9/2006 |
| EP | 1709980 | 10/2006 |
| EP | 1726315 A1 | 11/2006 |
| FR | 1497250 | 10/1967 |
| GB | 1033025 A | 6/1966 |
| JP | 56037070 | 4/1981 |
| JP | 56044060 | 4/1981 |
| JP | 56044061 | 4/1981 |
| JP | 56044062 | 4/1981 |
| JP | 56070865 | 6/1981 |
| JP | 57174173 | 10/1982 |
| JP | 01-223904 | 9/1989 |
| JP | 03-085169 | 4/1991 |
| JP | 03-085170 | 4/1991 |
| JP | 10216577 | 8/1998 |
| JP | 2001048254 | 2/2001 |
| JP | 2002068344 | 3/2002 |
| JP | 2002113398 | 4/2002 |
| JP | 2003246380 | 9/2003 |
| JP | 2003311191 | 11/2003 |
| JP | 2005081223 | 3/2005 |
| WO | WO 91/15409 A1 | 10/1991 |
| WO | WO 95/19304 A1 | 7/1995 |
| WO | WO95/29106 | 11/1995 |
| WO | WO 99/34266 A1 | 7/1999 |
| WO | WO 00/47335 A1 | 8/2000 |
| WO | WO 00/64802 A1 | 11/2000 |
| WO | WO00/75046 | 12/2000 |
| WO | WO 00/75046 A1 | 12/2000 |
| WO | WO 00/78467 A1 | 12/2000 |
| WO | WO 01/26448 A1 | 4/2001 |
| WO | WO 02/40177 A1 | 5/2002 |
| WO | WO 02/40376 A1 | 5/2002 |
| WO | WO 02/072161 A1 | 9/2002 |
| WO | WO 02/079679 A1 | 10/2002 |
| WO | WO 02/087976 A2 | 11/2002 |
| WO | WO 02/094014 A1 | 11/2002 |
| WO | WO03/037748 | 5/2003 |
| WO | WO 03/037748 A1 | 5/2003 |
| WO | WO03/037750 | 5/2003 |
| WO | WO 03/037750 A1 | 5/2003 |
| WO | WO03/042068 | 5/2003 |
| WO | WO 03/042068 A1 | 5/2003 |
| WO | WO03/062094 | 7/2003 |
| WO | WO 03/062094 A1 | 7/2003 |
| WO | WO03/062095 | 7/2003 |
| WO | WO 03/062095 A2 | 7/2003 |
| WO | WO 03/068412 A1 | 8/2003 |
| WO | WO 03/068413 A1 | 8/2003 |
| WO | WO03/082709 | 10/2003 |
| WO | WO 03/086902 A1 | 10/2003 |
| WO | WO 03/086947 A1 | 10/2003 |
| WO | WO 03/099682 A1 | 12/2003 |
| WO | WO 03/104109 A1 | 12/2003 |
| WO | WO 2004/043502 A1 | 5/2004 |
| WO | WO 2004/067963 A1 | 8/2004 |
| WO | WO 2004/073875 A2 | 9/2004 |
| WO | WO 2004/093927 A1 | 11/2004 |
| WO | WO 2004/093928 A2 | 11/2004 |
| WO | WO2005/011560 | 2/2005 |
| WO | WO2005/014060 | 2/2005 |
| WO | WO 2005/018691 A1 | 3/2005 |
| WO | WO 2005/023679 A1 | 3/2005 |

| | | |
|---|---|---|
| WO | WO2005/027630 | 3/2005 |
| WO | WO2005/048718 | 6/2005 |
| WO | WO2005/070474 | 8/2005 |
| WO | WO 2005/072059 A2 | 8/2005 |
| WO | WO 2005/072522 A1 | 8/2005 |
| WO | WO2005/079583 | 9/2005 |
| WO | WO2005/084721 | 9/2005 |
| WO | WO2006/005962 | 1/2006 |
| WO | WO 2006/012248 A1 | 2/2006 |
| WO | WO2006/013321 | 2/2006 |
| WO | WO2006/013322 | 2/2006 |
| WO | WO 2006/044416 A2 | 4/2006 |
| WO | WO2006/051267 | 5/2006 |
| WO | WO2006/054103 | 5/2006 |
| WO | WO2006/056762 | 6/2006 |
| WO | WO2006/058433 | 6/2006 |
| WO | WO2006/064187 | 6/2006 |
| WO | WO 2006/074454 | 7/2006 |
| WO | WO2006/087514 | 8/2006 |
| WO | WO2006/087515 | 8/2006 |
| WO | WO2006/095131 | 9/2006 |
| WO | WO 2006/104993 A2 | 10/2006 |
| WO | WO 2006/105652 A1 | 10/2006 |
| WO | WO 2006/108043 A2 | 10/2006 |
| WO | WO2006/134353 | 12/2006 |
| WO | WO2007/028954 | 3/2007 |
| WO | WO 2007/029044 A1 | 3/2007 |
| WO | WO2007/036724 | 4/2007 |
| WO | WO2007/045826 | 4/2007 |
| WO | WO2007/045827 | 4/2007 |
| WO | WO2007/045828 | 4/2007 |
| WO | WO2007/045831 | 4/2007 |
| WO | WO2007/045832 | 4/2007 |
| WO | WO2007/045834 | 4/2007 |
| WO | WO2007/045835 | 4/2007 |
| WO | WO2007/045859 | 4/2007 |
| WO | WO 2007/052016 A2 | 5/2007 |
| WO | WO 2007/064188 A1 | 6/2007 |
| WO | WO 2007/064189 A1 | 6/2007 |
| WO | WO 2007/064197 A1 | 6/2007 |
| WO | WO 2007/064199 A1 | 6/2007 |

OTHER PUBLICATIONS

International Search Report and Written Opinion in PCT/US2008/009663 dated Dec. 23, 2008.
PCT/US2008/009661 International Search Report and Written Opinion dated Nov. 13, 2008.

* cited by examiner

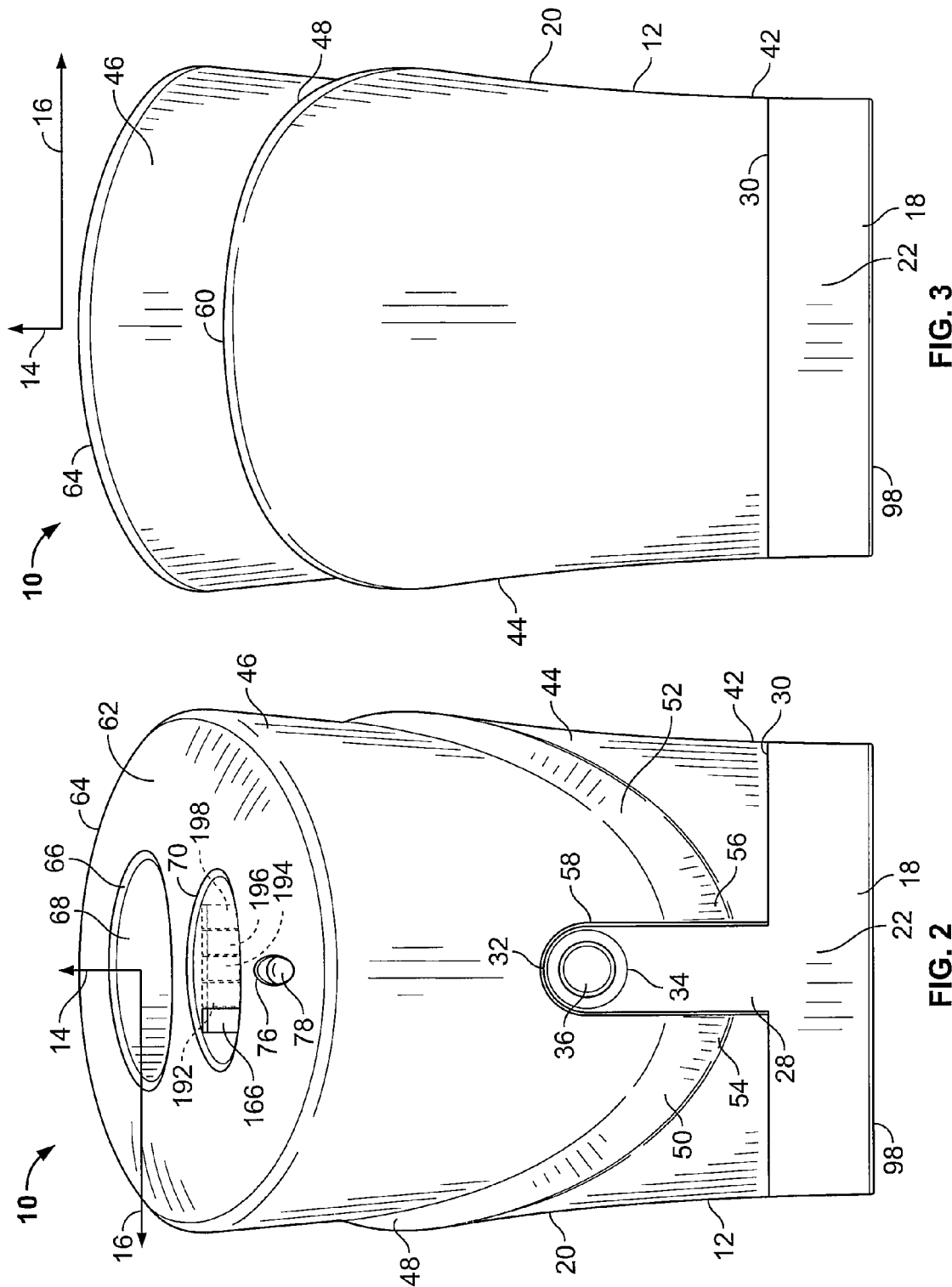

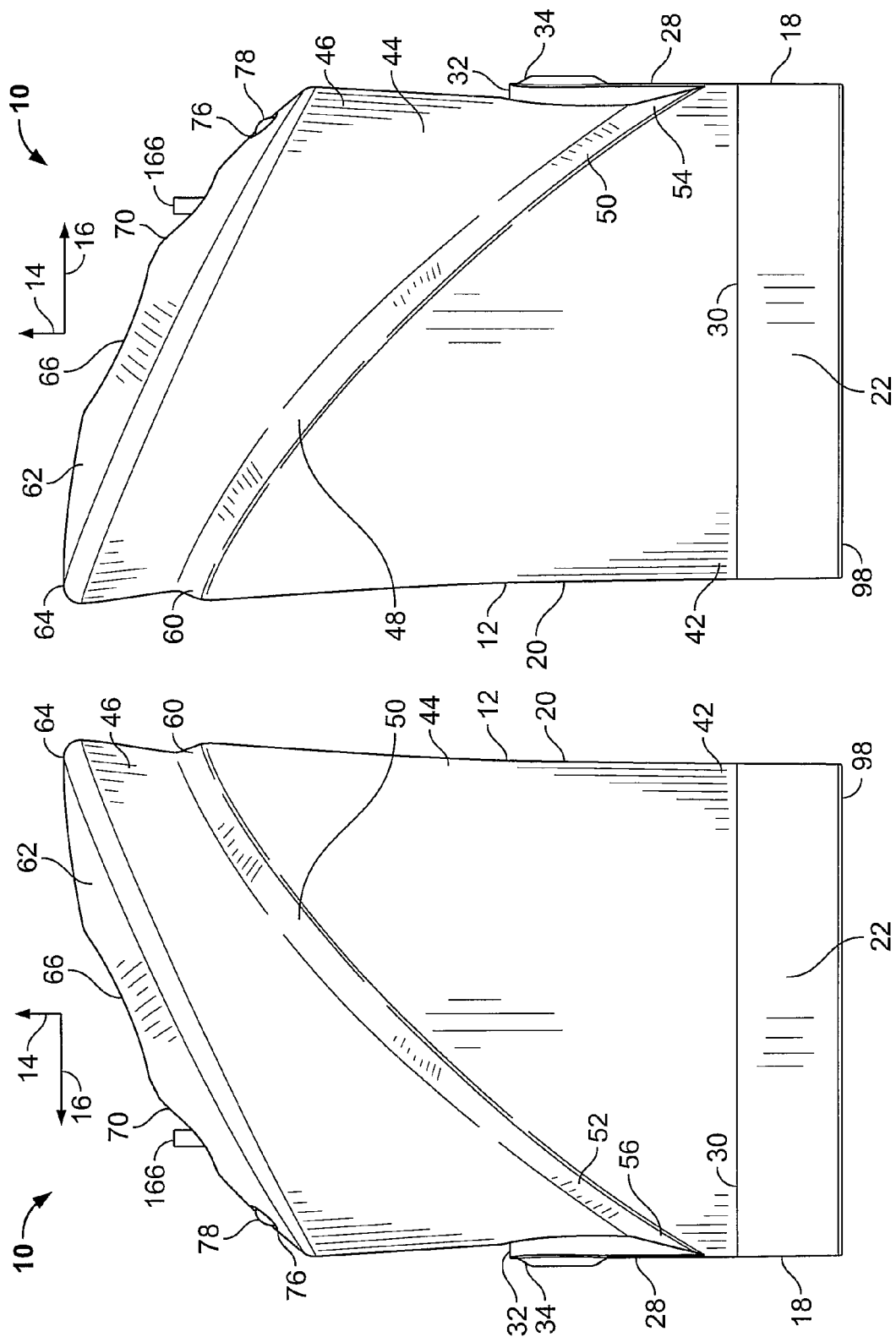

US 8,381,951 B2

OVERCAP FOR A SPRAY DEVICE

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present disclosure relates generally to an overcap for a container, and more particularly to an overcap adapted to be placed on an aerosol container having a tilt-activated valve stem.

2. Description of the Background of the Invention

Aerosol containers are commonly used to store and dispense volatile materials such as air fresheners, deodorants, insecticides, germicides, decongestants, perfumes, and the like. The volatile material is stored under compression and typically in a liquid state within a container. A release valve on the container controls release of the volatile material contained under compression therein. The release valve typically has a valve stem that outwardly extends from the valve, wherein the valve is activated by the valve stem and the volatile material flows out of the container through the valve stem. In such a release valve, the valve is activated by a displacement of the valve stem with respect to a valve body. The valve stem may be displaced along a longitudinal axis of the valve stem, i.e., axially, or the valve stem may be tilted or displaced in a direction transverse to the longitudinal axis of the valve stem, i.e., radially.

Activation of a release valve may be accomplished by an automated system or manually. In manual activation, a user may adjust an activation force applied to the valve as required to achieve a desired release. Therefore, consideration of applied force requirements is generally less important to design of manually activated release valves. Conventional actuator mechanisms may include motor driven linkages that apply downward pressure to depress the nozzle and open the valve within the container. Typically, these actuator mechanisms are unwieldy and are not readily adaptable to be used in a stand-alone manner and a hand-held manner. Further, many of these actuator mechanisms exhibit a great deal of power consumption. Generally, valves having tilt-activated valve stems require less force for activation than valves having vertically activated valve stems. Release valves requiring smaller activation forces are advantageous because such valves require less power to activate. Decreased power consumption will allow for longer power source life times. Smaller activation forces are also advantageous for automated activation because smaller required forces allow for simpler, smaller, and/or less costly automated designs.

Existing automated valve activation systems for valves having tilt-activated valve stems are complex and may be difficult to manufacture. Complex systems including gears, springs, and precise interactions of a multitude of moving parts may also be expensive to manufacture and too large to fit in an overcap for a container. Complex systems may also require more power to operate and may have a greater tendency to break than systems of simpler construction.

SUMMARY OF THE INVENTION

According to one aspect of the invention, a dispensing system includes a tilt-activated valve stem operably connected to a valve on a container and a vibe motor in communication with the valve stem. The vibe motor is adapted to impart radial motion to the valve stem upon activation.

According to another aspect of the invention, an overcap for a volatile material container includes a housing adapted to be mounted on a container having a tilt-activated valve stem operably connected to a valve. A vibe motor is disposed within the housing. The vibe motor is adapted to impart radial displacement to the valve stem.

According to yet another aspect of the invention, an overcap for a volatile material container includes a housing adapted to be mounted on a container having a tilt-activated valve stem operably connected to a valve. A vibe motor is disposed within the housing. The vibe motor is adapted to impart radial displacement to the valve stem upon activation in response to a signal from at least one of a timer, a sensor, or a manual activator.

In a different aspect of the invention, a method of dispensing a fluid includes the step of providing a tilt-activated valve stem operably connected to a valve on a container. A different step includes providing oscillatory motion to the valve stem, wherein the oscillatory motion imparts radial motion to the valve stem.

In another aspect of the invention, a dispensing system includes a tilt-activated valve stem operably connected to a valve on a container. An actuation mechanism is in oscillatory communication with the valve stem. The actuation mechanism is adapted to impart radial motion to the valve stem upon activation.

In still a different aspect of the invention, a dispensing system includes a tilt-activated valve stem operably connected to a valve on a container. The tilt-activated valve stem is disposed in a non-actuation position during a non-activation state. The tilt-activated valve stem is moved between a first actuation position and a second actuation position during an activation state. The first and second actuation positions are offset radially from the non-actuation position.

BRIEF DESCRIPTION OF THE DRAWINGS

FIG. 2 is a front elevational view of the overcap of FIG. 1;

FIG. 3 is a rear elevational view of the overcap of FIG. 1;

FIG. 4 is a right side elevational view of the overcap of FIG. 1;

FIG. 5 is a left side elevational view of the overcap of FIG. 1;

Other aspects and advantages of the present invention will become apparent upon consideration of the following detailed description, wherein similar structures have similar reference numerals.

DETAILED DESCRIPTION

Figure 1:
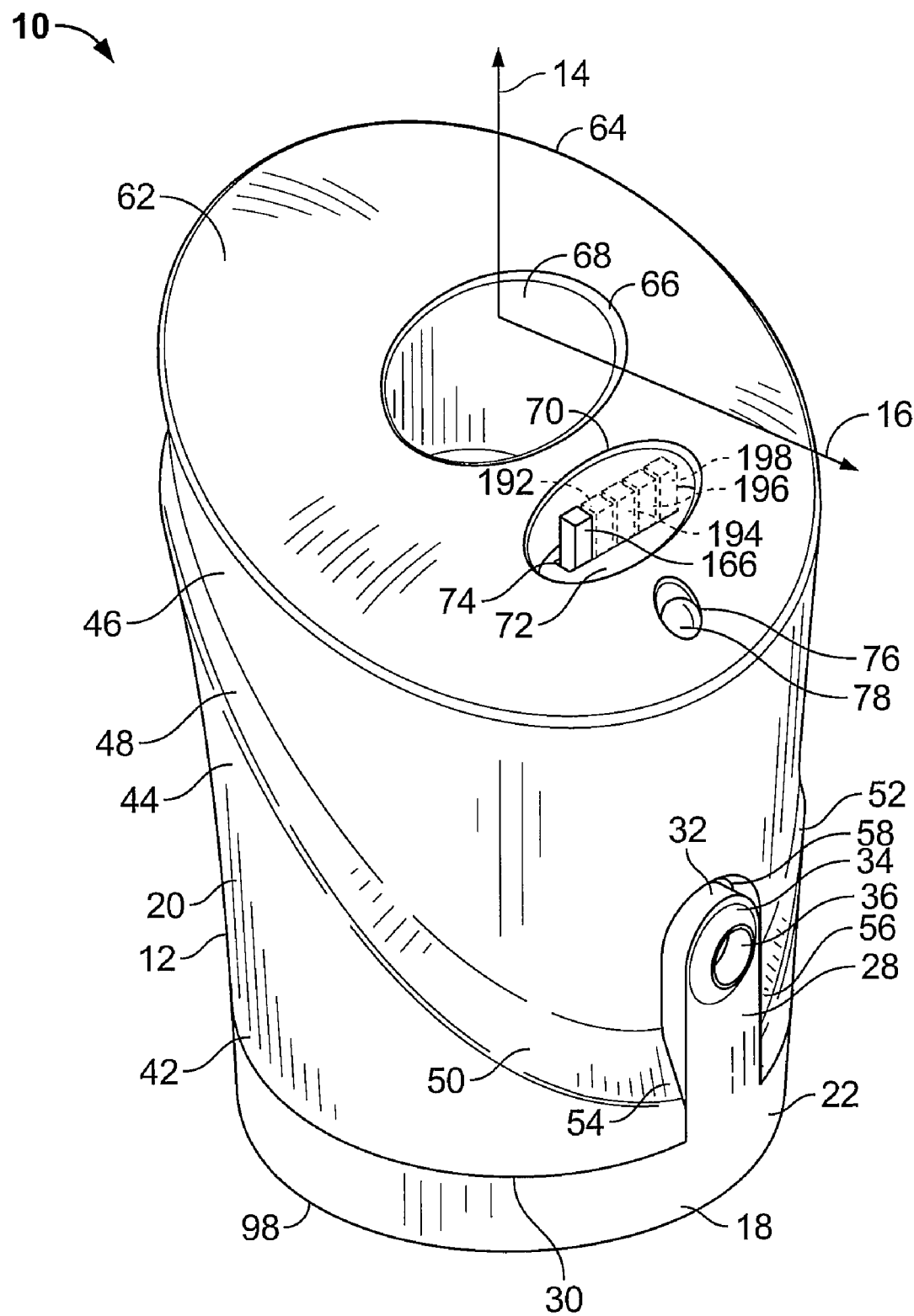
FIG. 1 is an isometric view of one embodiment of an actuator overcap.
Figure 6:
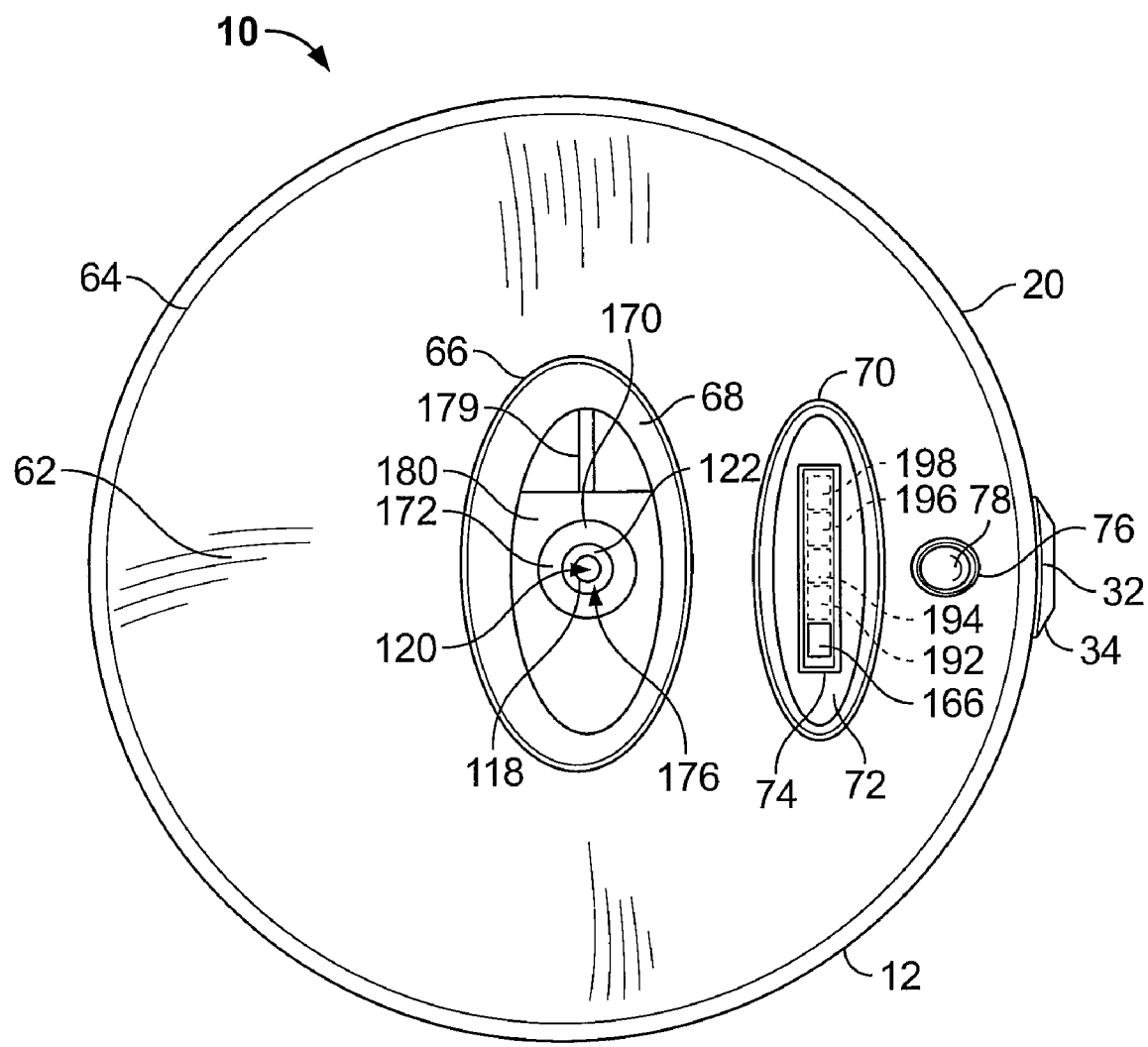
FIG. 6 is a top plan view of the overcap of FIG. 1.
Figure 7:
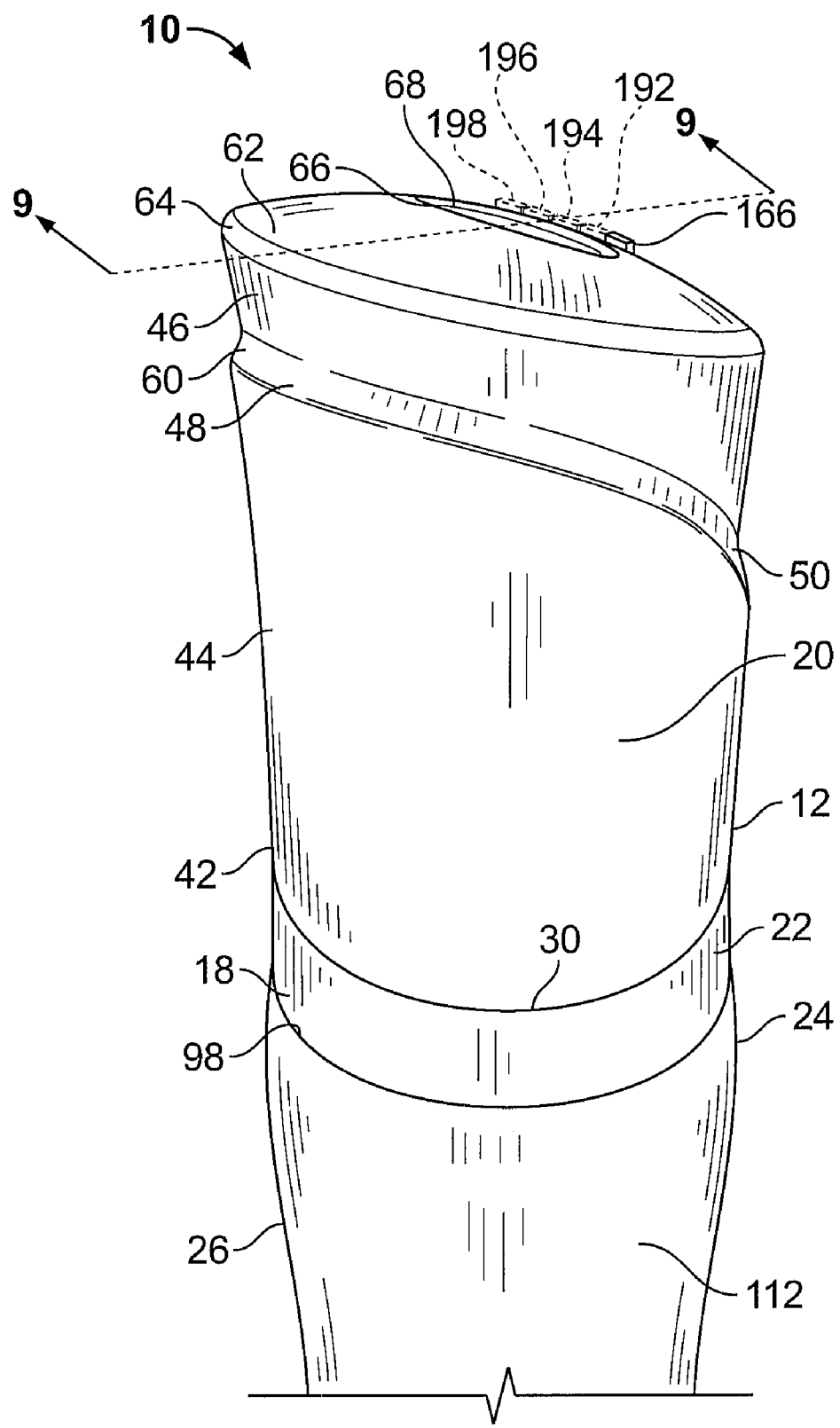
FIG. 7 is an isometric view of the overcap of FIG. 1 mounted on a fluid container.
Figure 8:
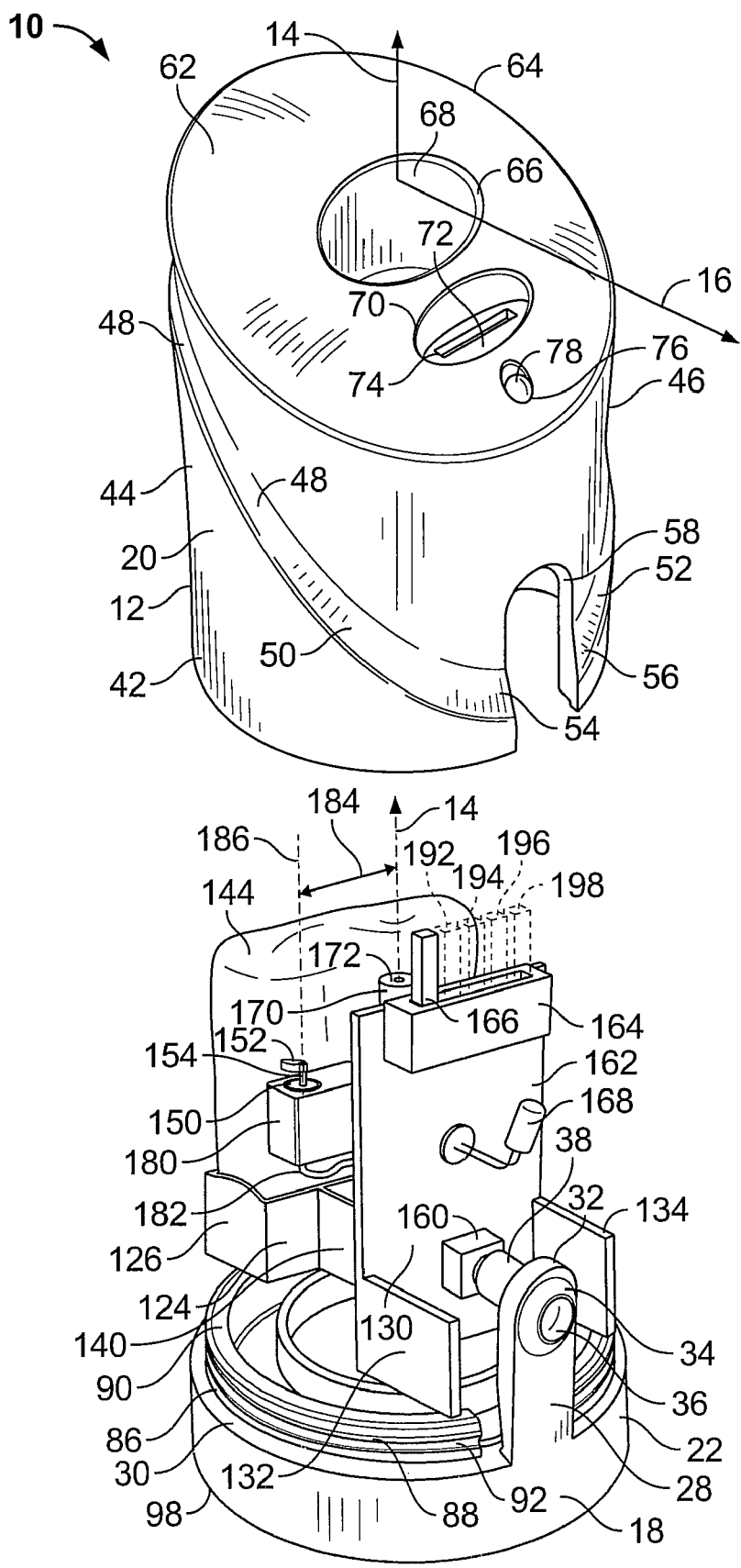
FIG. 8 is an exploded isometric view of the overcap of FIG. 1.

FIGS. 1-6 depict an actuator overcap 10 having a generally cylindrical housing 12 that has a longitudinal dimension along a longitudinal axis 14 and a radial dimension along a radial axis 16. The housing 12 includes a base portion 18 and a removable cap 20. The base portion 18 comprises a cylindrical section 22 adapted to be retained on an upper end 24 of a conventional aerosol container 26, which is shown in FIG. 7, and will be described in further detail below. A post 28 extends upwardly from a top end 30 of the cylindrical section 22. The post 28 includes a curved distal end 32 with an oval pushbutton 34 on an outer wall thereof. The pushbutton 34 is further provided with a concave depression 36. A cylindrical rod 38 (see FIG. 8) is provided on an inner wall 40 (see FIG. 9) of the post 28 generally opposite the pushbutton 34.

The removable cap 20 includes a cylindrical bottom portion 42, which has a diameter substantially equal to that of the top end 30 of the cylindrical section 22. A sidewall 44 extends between the bottom portion 42 of the removable cap 20 and a top portion 46 thereof. The sidewall 44 tapers outwardly about the longitudinal axis 14 of the removable cap 20 so that a cross-sectional diameter of the removable cap adjacent the bottom portion 42 is smaller than a cross-sectional diameter of the removable cap 20 adjacent the top portion 46. The uniform tapering of the removable cap 20 is truncated by a stepped portion 48. The stepped portion 48 includes first and second tapered surfaces 50, 52, respectively, that extend inwardly toward the longitudinal axis 14 of the removable cap 20. The first and second tapered surfaces 50, 52 include first ends 54, 56, respectively, disposed on opposing sides of a groove 58 adjacent the bottom portion 42 of the removable cap 20. The tapered surfaces 50, 52, curve upwardly from the first ends 54, 56 toward a portion 60 of the removable cap 20 opposite the groove 58 and adjacent the top portion 46.

An upper surface 62 of the removable cap 20 is convex and is bounded by a circular peripheral edge 64. An elliptical shaped discharge orifice 66 is centrally disposed within the upper surface 62. A frusto-conical wall 68 depends downwardly into an interior of the removable cap 20 about a periphery of the discharge orifice 66. A curved groove 70 is disposed between the discharge orifice 66 and the peripheral edge 64. The groove 70 includes a flat bottom 72 with a rectangular notch 74 disposed therein. An aperture 76 is also provided between the groove 70 and the peripheral edge 64. A light transmissive rod 78 is held within the aperture 76 by an interference fit.

Figure 9:
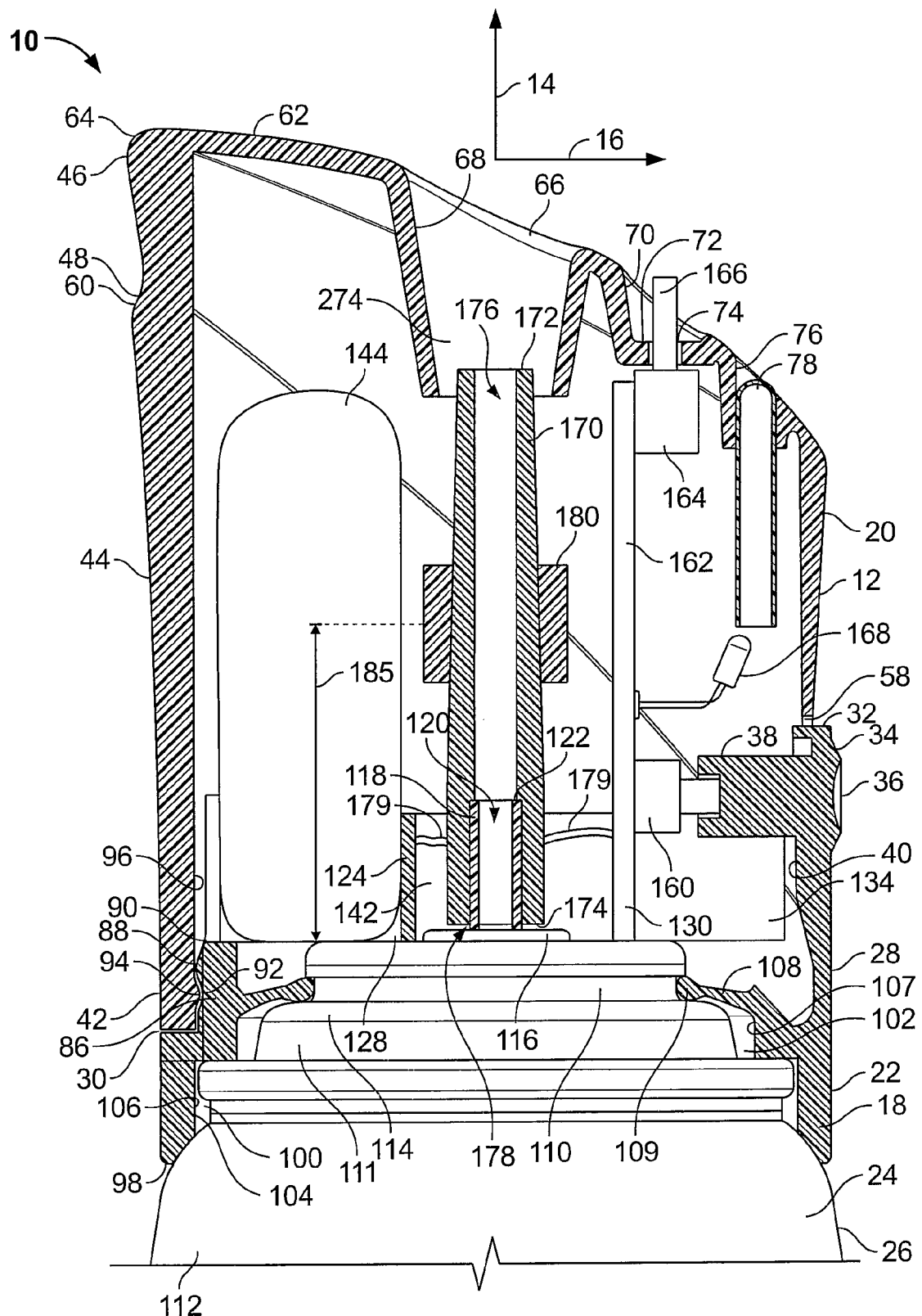
FIG. 9 is an enlarged partial sectional view taken generally along the lines 9-9 of FIG. 7.
Figure 10:
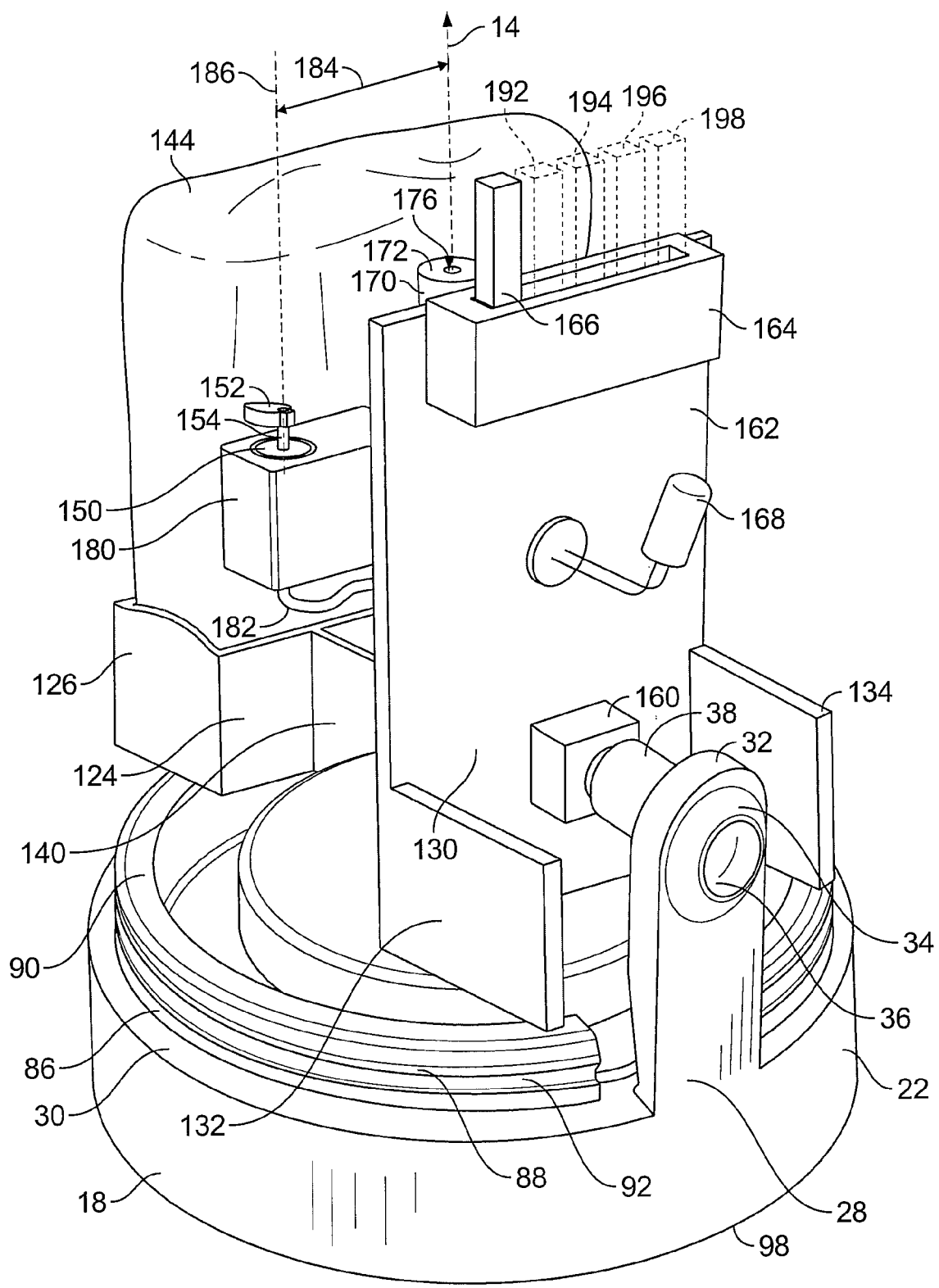
FIG. 10 is an isometric view of the overcap of FIG. 1 with a portion of a housing removed.

As shown in FIGS. 8-12C, the base portion 18 includes a platform 86 that is disposed on the top end 30 of the cylindrical section 22. The platform 86 is sized to frictionally engage with the bottom portion 42 of the removable cap 20 when the removable cap is attached to the base portion 18. FIG. 9 illustrates that the platform 86 comprises an inwardly stepped portion, which includes a sidewall 88 and a top portion 90. The sidewall 88 includes a circumferential notch 92 adapted to fittingly receive an annular portion 94 on an inner wall 96 of the removable cap 20 adjacent the bottom portion 42 thereof. Further, additional retention support is provided by the groove 58, which is sized to fittingly receive the post 28 when the removable cap 20 is placed on the base portion 18. During the placement of the removable cap 20 on the section 22, the user aligns the groove 58 with the post 28 and slides the removable cap 20 downwardly until same contacts the top end 30 of the base portion 18 and forms an interference fit with the platform 86.

A bottom end 98 of the base portion 18 is also shaped to fit on the upper end 24 of the aerosol container 26. FIG. 9 shows that the present embodiment includes recesses 100, 102 around an inner circumference 104 of the base portion 18. The recess 100 is defined by a surface 106 and the recess 102 is defined by a surface 107, which includes an annular portion 108 that projects inwardly therefrom. A distal end 109 of the annular portion 108 forms a snap fit with an undercut 110 of a mounting cup 111 of the aerosol container 26. The surface 106 forms an interference fit with portions of the aerosol container 26 beneath the mounting cup 110. The snap fit between the annular portion 108 and the undercut 110 and the interference fit between the surface 106 and portions of the aerosol container 26 assist in securely mounting the base portion 18 to the aerosol container 26. Further, contact between the bottom end 98 of the base portion 18 and the upper end 24 of the aerosol container 26 may assist in preventing rocking or shifting of the base portion 18 when mounted on the aerosol container 26.

In another embodiment of the overcap 10, the removable cap 20 and the base portion 18 form an integral unit that is attached to the upper end 24 of the aerosol container 26 by an interference fit. Indeed, regardless of whether the housing 12 comprises one or more components, the housing 12 may be retained on the aerosol container 26 in any manner known by those skilled in the art. For example, the overcap retention structures described in Balfanz U.S. Pat. No. 4,133,408, Demarest U.S. Pat. No. 5,027,982, and Demarest et al. U.S. Pat. No. 5,609,605, which are herein incorporated by reference in their entirety, may be used in connection with any of the embodiments described herein. Further, any of the aesthetic aspects of the overcap 10 described herein may be modified in any manner known by one skilled in the art, e.g., the stepped portion 48 could be removed or the housing 12 could be provided with a different shape.

The overcap 10 discharges fluid from the aerosol container 26 upon the occurrence of a particular condition. The condition could be the manual activation of the overcap 10 or the automatic activation of the overcap 10 in response to an electrical signal from a timer or a sensor. The fluid discharged may be a fragrance or insecticide disposed within a carrier liquid, a deodorizing liquid, or the like. The fluid may also comprise other actives, such as sanitizers, air fresheners, odor eliminators, mold or mildew inhibitors, insect repellents, and/ or the like, and/or that have aromatherapeutic properties. The fluid alternatively comprises any fluid known to those skilled in the art that may be dispensed from a container. The overcap 10 is therefore adapted to dispense any number of different fluid formulations.

Still referring to FIG. 9, the container 26 may be an aerosol container of any size and volume known to those skilled in the art. However, the container 26 preferably comprises a body 112 (see FIG. 13) with the mounting cup 110 crimped to the upper end 24 thereof. The mounting cup 110 is generally cylindrical in shape and includes an outer wall 114 that extends circumferentially therearound (see FIG. 9). A pedestal 116 extends upwardly from the mounting cup 110. A valve assembly (not shown) within the container 26 includes a valve stem 118 extending upwardly from the pedestal 116. A bore 120 extends from the valve assembly through the valve stem 118. The valve stem 118 is of the tilt-activated type similar to the one described in Van der Heijden U.S. Pat. No. 4,064,782, which is herein incorporated by reference in its entirety.

When a distal end of the valve stem 118 is tilted radially to a sufficient degree, i.e., into an operable position, the valve assembly is opened and the contents of the container 26 are discharged from a discharge end 122 of the valve stem 118. In the terminology of the axisymmetric coordinate system used herein, a radial displacement includes any displacement of the distal end of the valve stem 118 away from the longitudinal axis 14. Such a radial displacement may therefore be characterized as a lateral or a transverse displacement of the distal end of the valve stem 118. The contents of the container 26 may be discharged in a continuous or metered dose. Further, the discharging of the contents of the container 26 may be effected in any number of ways, e.g., a discharge may comprise a partial metered dose or multiple consecutive discharges.

Referring to FIGS. 8-12C, a first transverse wall 124 is provided with first and second frame members 126, 128 on opposing sides thereof. The first and second frame members 126, 128 are attached to the top portion 90 of the platform 86. A second transverse wall 130 is provided with third and fourth frame members 132, 134 that extend from opposing sides thereof and that are similarly attached to the top portion 90 of the platform 86. Third and fourth transverse walls 140, 142 are also provided to add rigidity to the structure of the base 18.

Figure 13:
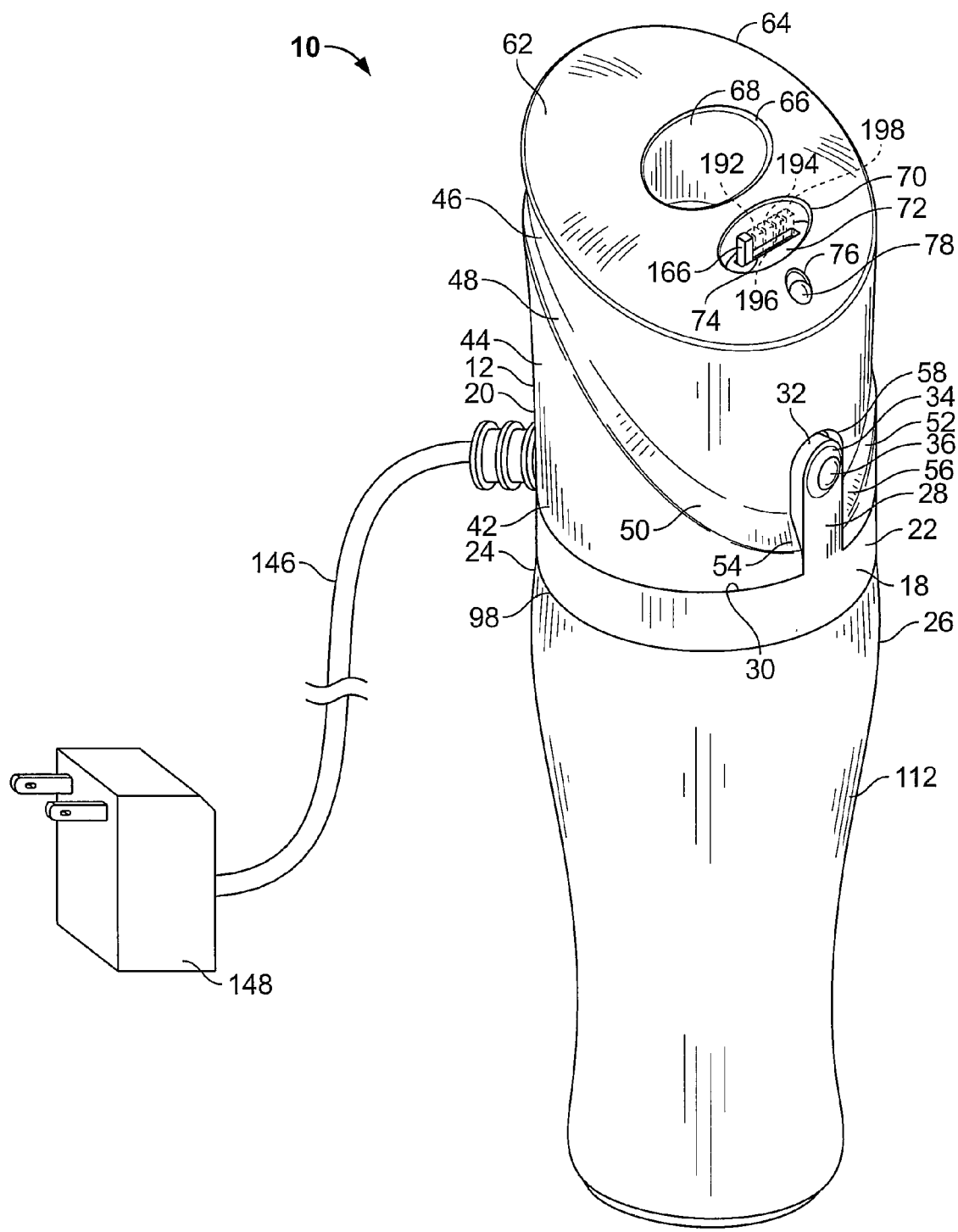
FIG. 13 is another embodiment of an overcap similar to the one depicted in FIG. 7, which includes an A.C. power connector.

The first and second frame members 126, 128 are adapted to retain a D.C. power source 144 comprising one or more AA or AAA batteries therein. The power source 144 of the present embodiment is shown schematically to illustrate the interchangeability of the batteries with other power sources. In some embodiments, the batteries may be replaced by a rechargeable Nickel-Cadmium battery pack having an electrical lead 146 that may be used to connect the battery pack to an A.C. power outlet 148, such as seen in FIG. 13. In another embodiment, the D.C. power source 144 may be entirely replaced by an A.C. power adapter having an appropriate power transformer and A.C./D.C. converter as known to those of skill in the art.

Figure 14:
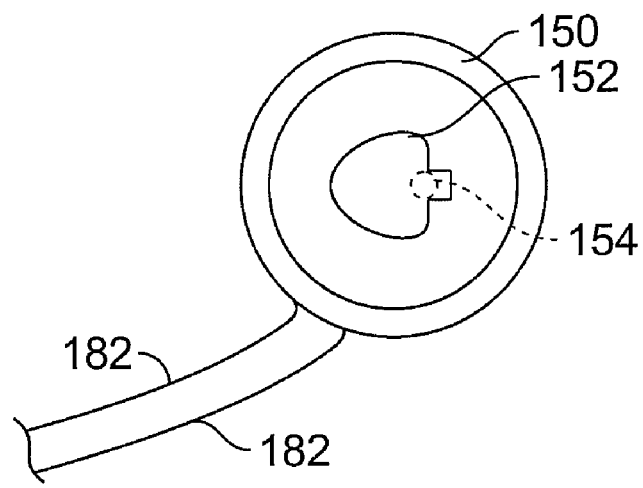
FIG. 14 is a top plan view of a vibe motor.
Figure 15:
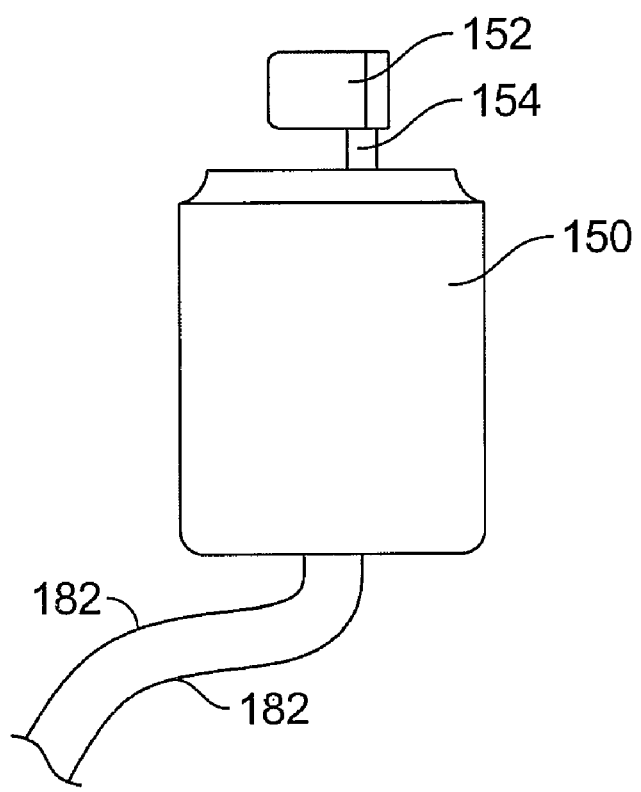
FIG. 15 is a front elevational view of the vibe motor of FIG. 14.

An actuation mechanism, e.g., a vibe motor 150 such as the one shown in FIGS. 14 and 15, is provided within the overcap 10. The vibe motor 150 is adapted to cause the discharge of fluid from the aerosol container 26. In the present embodiment, the vibe motor 150 includes a weighted head 152 that is eccentrically mounted to a shaft 154 of the vibe motor 150. Eccentric rotation of the weighted head 152 results in a dynamic imbalance of the vibe motor 150, which causes the vibe motor 150 to impart an oscillatory vibration to any member attached thereto. It is anticipated that numerous types of vibe motors having different structural and/or design characteristics may be used in connection with the present embodiments. However, it has been found advantageous to use a vibe motor small enough to fit within the housing 12 that can also generate enough force to displace the valve stem 118. A representative vibe motor, for example, is a Panasonic vibrating motor, with a model number KHN6, which is available from Panasonic Corporation of North America. The KHN6 motor weighs 1.15 grams, is rated at 1.3 volts and 70 milliamps, has a rotation speed of 7,000 revolutions per minute (rpm), and generates 0.76 Newtons (0.17 pounds) of force.

FIGS. 8-12C depict a normally open switch 160 disposed on a printed circuit board 162, which in the present embodiment comprises a portion of the second transverse wall 130. The switch 160 is operably aligned with the pushbutton 34 such that the manual depression of the pushbutton closes the open switch 160. Further, a user selectable switch assembly 164 is disposed adjacent a top portion of the printed circuit board 162. The user selectable switch assembly 164 includes a control member, for example, a finger 166 extending upwardly therefrom. The finger 166 may be used to select different operating modes (as discussed in greater detail below). The finger 166 fits within the notch 74 when the removable cap 20 is engaged with the base portion 18 such that a user may operatively interact with the finger 166 (see FIG. 1). The user selectable switch assembly 164 may be a linear displacement type switch controlled by a finger 166 as illustrated herein. However, the user selectable switch assembly could be rotational and controlled by a turning knob, or could have any other geometrical configuration and corresponding control mechanism as is known in the art. Further, a light emitting diode (LED) 168 disposed on the printed circuit board 162 is positioned proximate the light transmissive rod 78 of the removable cap 20 (see FIG. 9).

With particular reference to FIGS. 12A-12C, 16A, and 16B, a dispensing member 170 is shown. In the present embodiment, the dispensing member 170 comprises a cylindrical member having a discharge end 172 and a bottom end 174. A bore 176 extends from an opening 178 adjacent the bottom end 174 of the dispensing member 170 through the discharge end 172 thereof. The dispensing member 170 provides a continuous fluid connection between the valve assembly within the aerosol container 26 and the discharge end 172 of the dispensing member 170. The dispensing member 170 may be disposed on the valve stem 118 by a press fitting procedure or by any other manner known to one having skill in the art.

When the housing 12 is placed on the aerosol container 26, the distal end of the valve stem 118 is seated within the opening 178 adjacent the bottom end 174 of the dispensing member 170. The discharge end 172 of the dispensing member 170 is disposed adjacent to and/or within the frustoconical wall 68 depending from the discharge orifice 66 of the housing 12. The dispensing member 170 is appropriately centered to align the discharge end 172 of the dispensing member 170 with the discharge orifice 66. In other embodiments, the dispensing member 170 comprises a non-cylindrical shape and/or includes varying cross-sectional dimensions throughout an entire or partial length of the member 170, e.g., the discharge end 172 of the bore 176 may be narrower than other portions of the bore 176 or may be angled with respect to other portions of the bore 176. Further, all or part of the bores 120 and 176 that extend the lengths of the valve stem 118 and the dispensing member 170, respectively, may be cylindrical or any other shape, e.g., portions of the bore 176 adjacent the discharge end 172 thereof may be generally square in cross-section, whereas the remaining portions of the bore 176 may be generally circular in cross-section.

Figure 11:
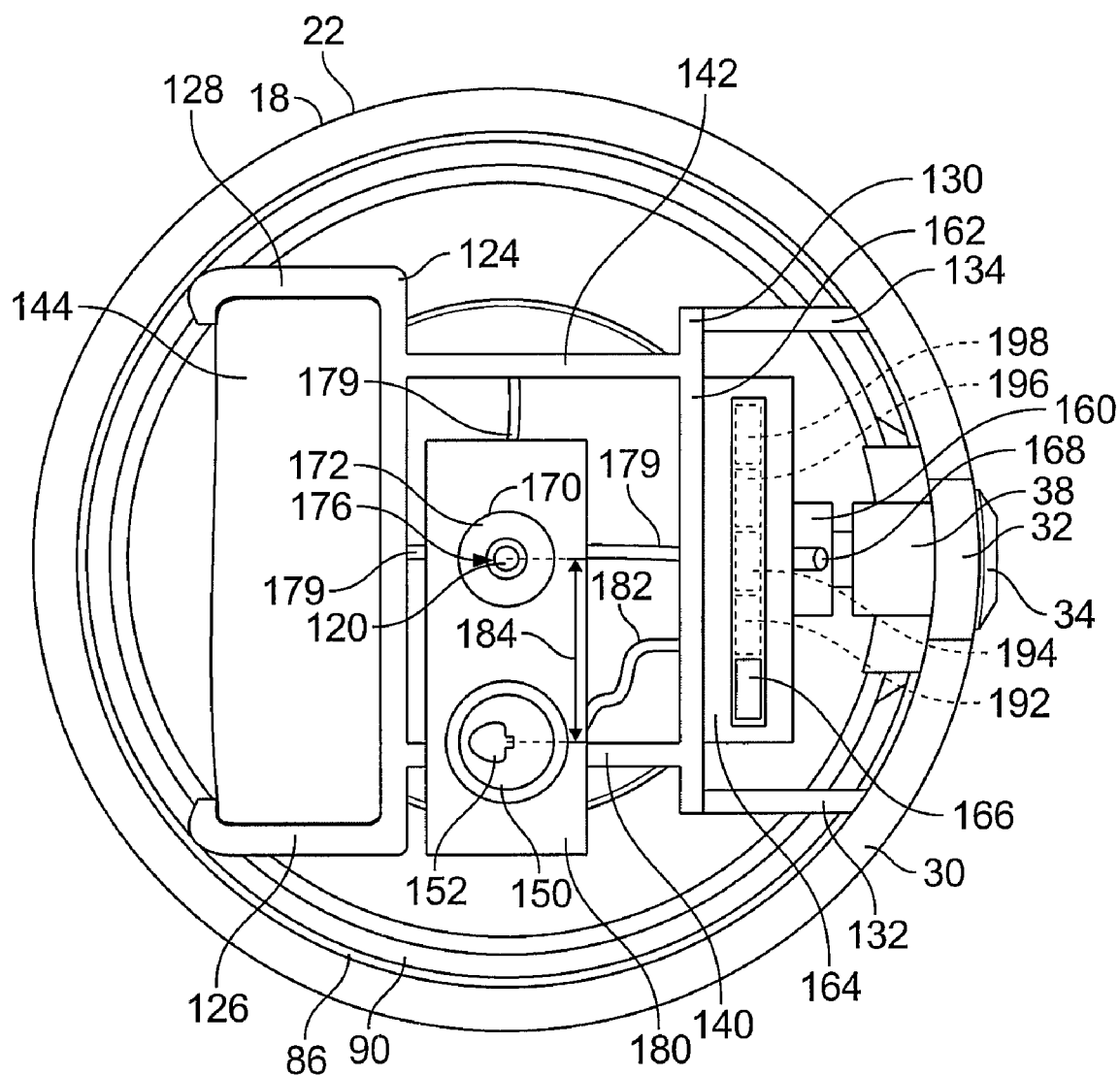
FIG. 11 is a top plan view of the overcap of FIG. 10.

It is also anticipated that the dispensing member 170 may be attached to the overcap 10. Attachment means of this nature provide the added benefit of a unitary overcap 10, which provides greater user convenience in handling and may assist in preventing the loss of the dispensing member 170. An additional benefit to having an attachment means connecting the dispensing member 170 to the overcap 10 is that the dispensing member 170 may be provided with a guiding function, i.e., as the overcap 10 is placed on the aerosol container 26 or the removable cap 20 is placed on the base portion 18, the dispensing member 170 interacts with the valve stem 118 to orient the overcap 10 and/or the removable cap 20 into an operable position. Alternatively, or in addition to, the placement of the overcap 10 onto the aerosol container 26 or the removable cap 20 onto the base portion 18 may provide an alignment function to guide the dispensing member 170 into engagement with the valve stem 118. In one embodiment, the bottom end 174 of the dispensing member 170 is flexibly attached to one or more of the first, second, third, or fourth transverse walls 124, 130, 140, 142. As shown in FIGS. 9, 11, 16A, and 16B, unstretched elastic strips 179 attach the dispensing member 170 to the transverse walls 124 and 130. FIGS. 6 and 11 show that the dispensing member 170 is also attached to the transverse wall 142 by another elastic strip 179. The elastic strips 179 are of sufficient strength to hold the dispensing member 170 affixed to the overcap 10. However, the elastic strips 179 are attached to the dispensing member 170 in a manner that minimally interferes with the dynamic response of the dispensing member 170 when driven by the vibe motor 150. The dispensing member 170 may alternatively be attached to the overcap 10 by other methods known to those of ordinary skill in the art.

In the present embodiment, the vibe motor 150 is attached to the dispensing member 170 in oscillatory communication with the valve stem 118, i.e., the vibe motor 150 is provided within the overcap 10 so that vibratory movement of the vibe motor 150 will directly or indirectly displace the valve stem 118. The vibe motor 150 may be connected directly to the dispensing member 170, or may be connected to the dispensing member 170 by a coupling member 180. The coupling member 180 may be attached to the dispensing member 170 by a press fit, an adhesive, or by any other method known to one having skill in the art. Similarly, the vibe motor 150 may be attached to the coupling member 180 by a press fit, an adhesive, or by any other method known to one having skill in the art. In another embodiment, the vibe motor 150 may be connected to the valve stem 118 by the coupling member 180. It is envisioned that numerous other connection arrangements are possible, e.g., the vibe motor 150 could be directly connected to the valve stem 118 or mounted to another structure in vibratory communication with the valve stem 118. Wires 182 connect the printed circuit board 162 to the vibe motor 150.

Figure 16A:
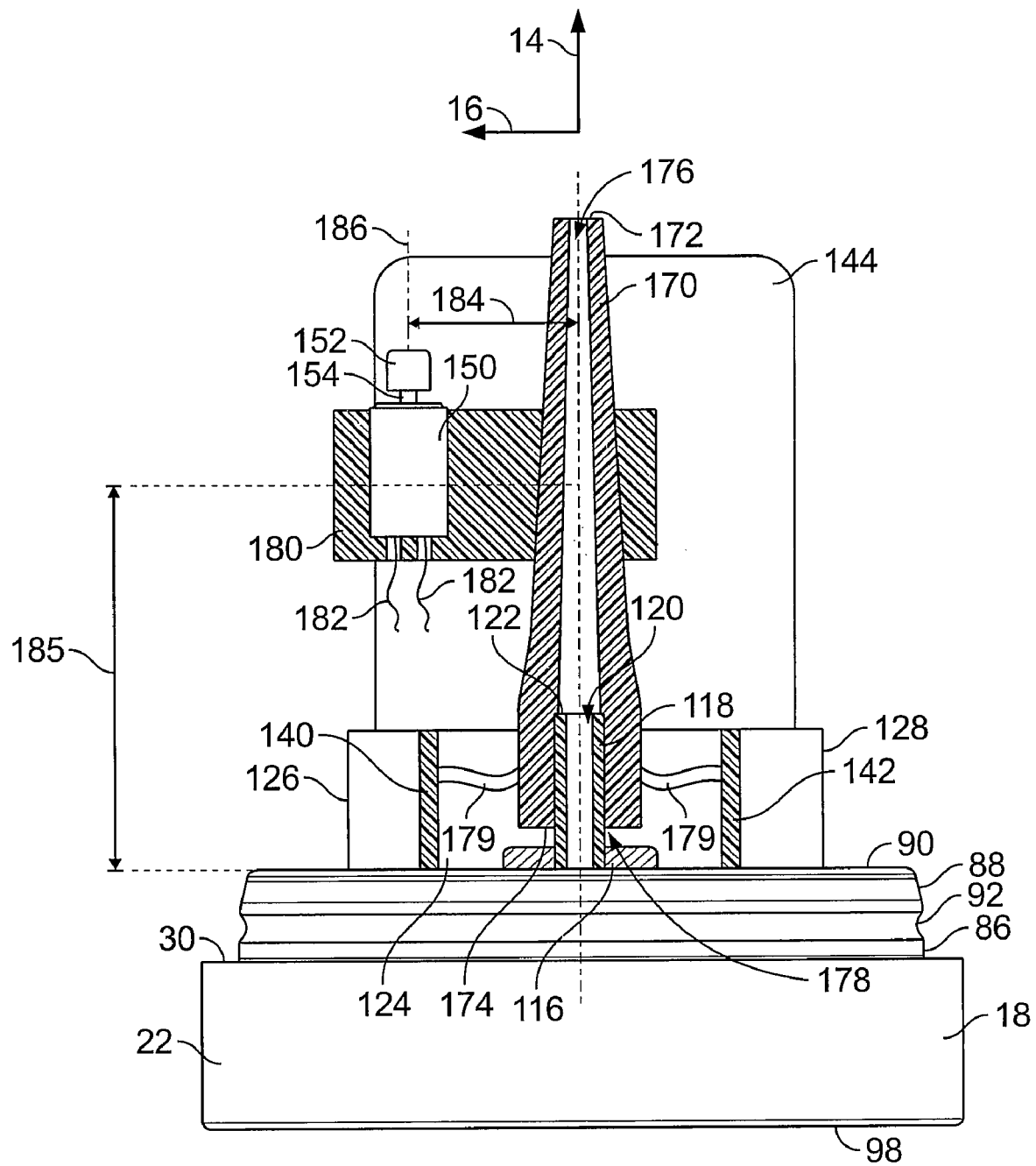
FIG. 16A is a partial sectional view taken generally along the lines 16-16 of FIG. 12A that further includes a portion of a fluid container and that illustrates the first orientation of the vibe motor shown in FIG. 12A.
Figure 16B:
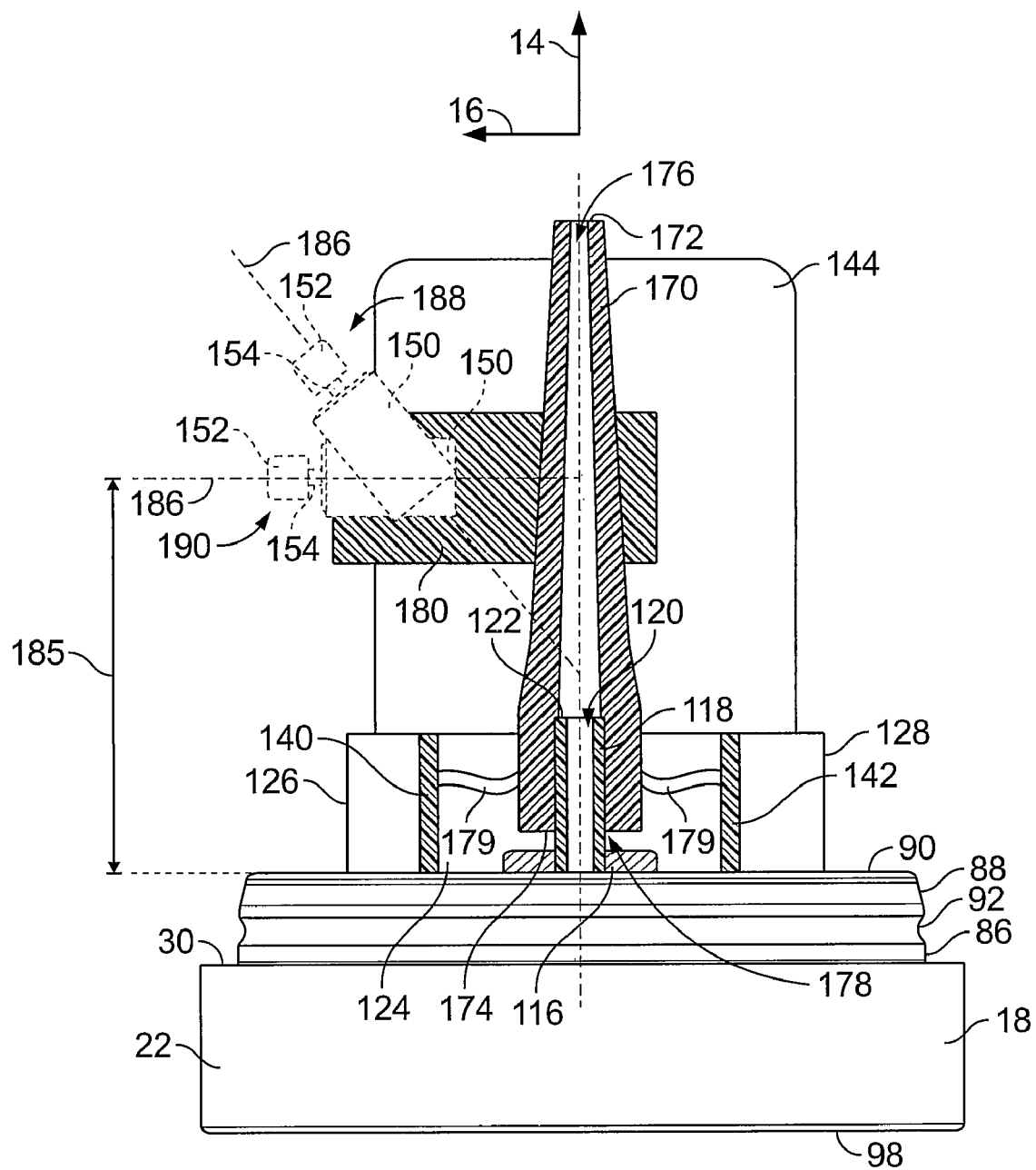
FIG. 16B is a partial sectional view taken generally along the lines 16-16 of FIG. 12A that further includes a portion of a fluid container and that illustrates fourth and fifth orientations of a vibe motor with wires omitted for purposes of clarity.

When the vibe motor 150 is not activated, the dispensing member 172 is aligned coincident with the longitudinal axis 14. Vibration of the vibe motor 150 generates a force that acts through a moment arm to deliver an amount of torque to the valve stem 118, thereby activating the valve stem 118 to discharge the contents of the aerosol container 26. The vibe motor 150 is mounted to the dispensing member 170 offset from the longitudinal axis 14 by a distance 184, as shown in FIGS. 8, 10, 11, and 16A. An axis of rotation 186 of the shaft 154 is oriented parallel with the longitudinal axis 14, as shown in FIGS. 8, 10, 12A, and 16A. The vibe motor 150 may be mounted approximately near the center of the dispensing member 170. Alternatively, the vibe motor 150 may be mounted adjacent the bottom end 174 or the discharge end 172 of the dispensing member 170, or anywhere therebetween. A distance 185, measured between a mounting point of the vibe motor 150 and a base of the tilt-activated valve stem 118, as shown in FIGS. 9, 16A, and 16B, preferably varies within a range from about 0.25 in. to about 2 in. Further, the distance 184 preferably varies within a range from about 0.25 in. to about 1 in. The effective length of the moment arm is determined by a geometric combination of the lengths 184 and 185 and an orientation of the vibe motor 150. For example, by mounting the vibe motor 150 closer to the discharge end 172 of the dispensing member 170, a longer moment arm is provided through which force generated by the vibe motor 150 is transferred to the valve stem 118. The effective length of the moment arm is one of several factors that determines the amount of torque applied to the base of the tilt-activated-valve stem 118 and therefore a rate of discharge of the contents of the aerosol container 26.

Figure 12A:
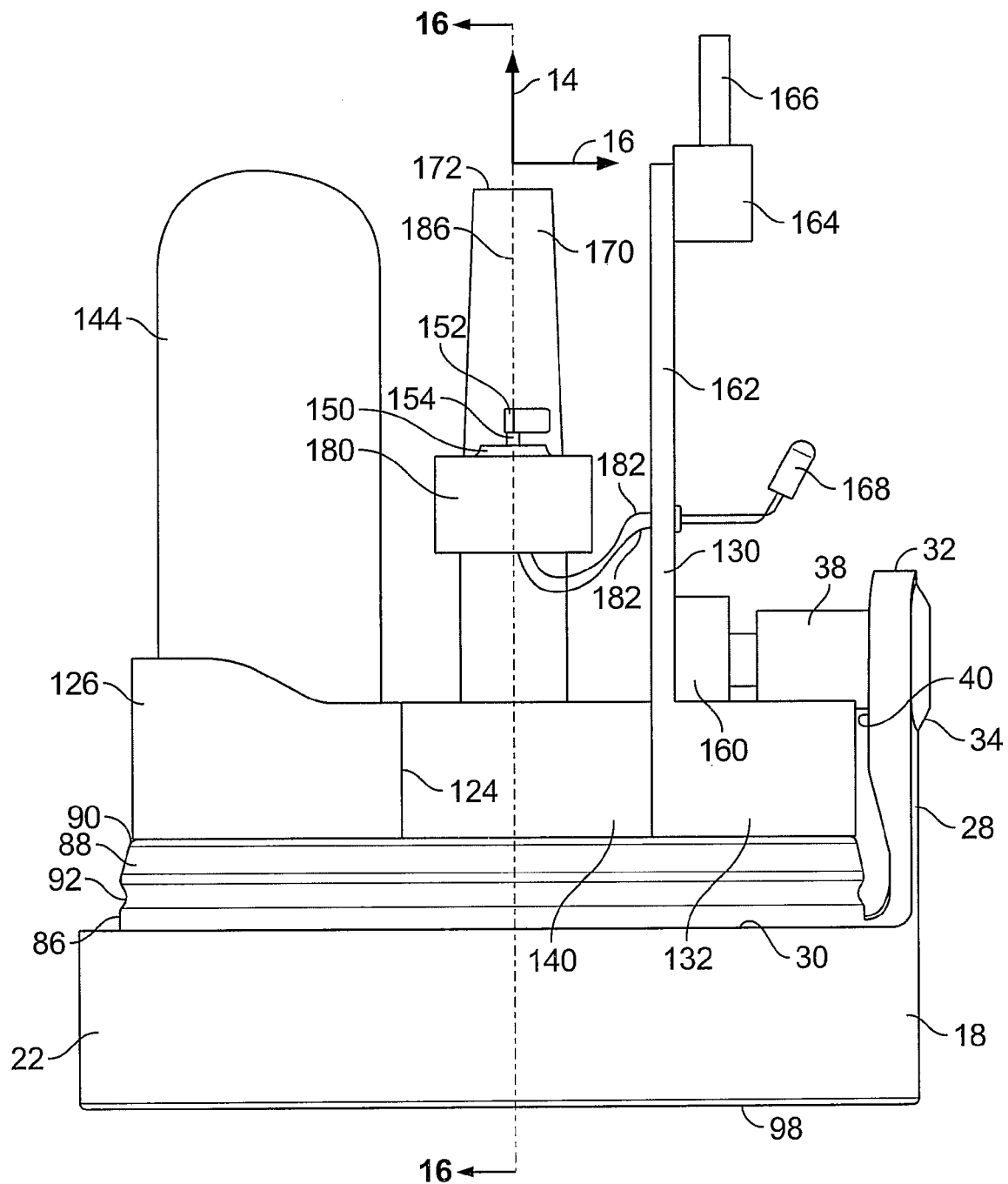
FIG. 12A is a left side elevational view of the overcap of FIG. 10 illustrating a first orientation of a vibe motor.
Figure 12B:
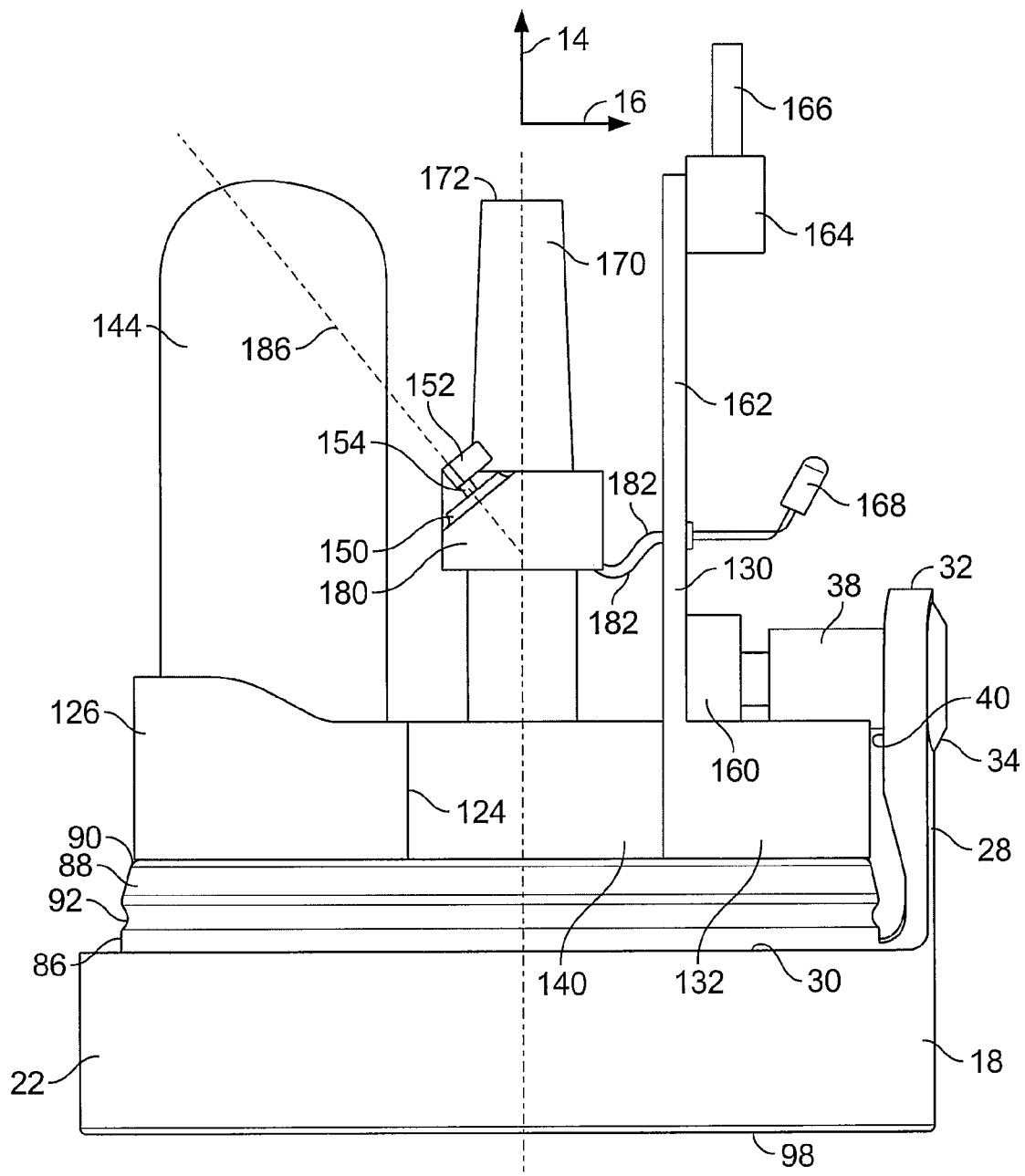
FIG. 12B is a is a left side elevational view of the overcap of FIG. 10 illustrating a second orientation of a vibe motor.
Figure 12C:
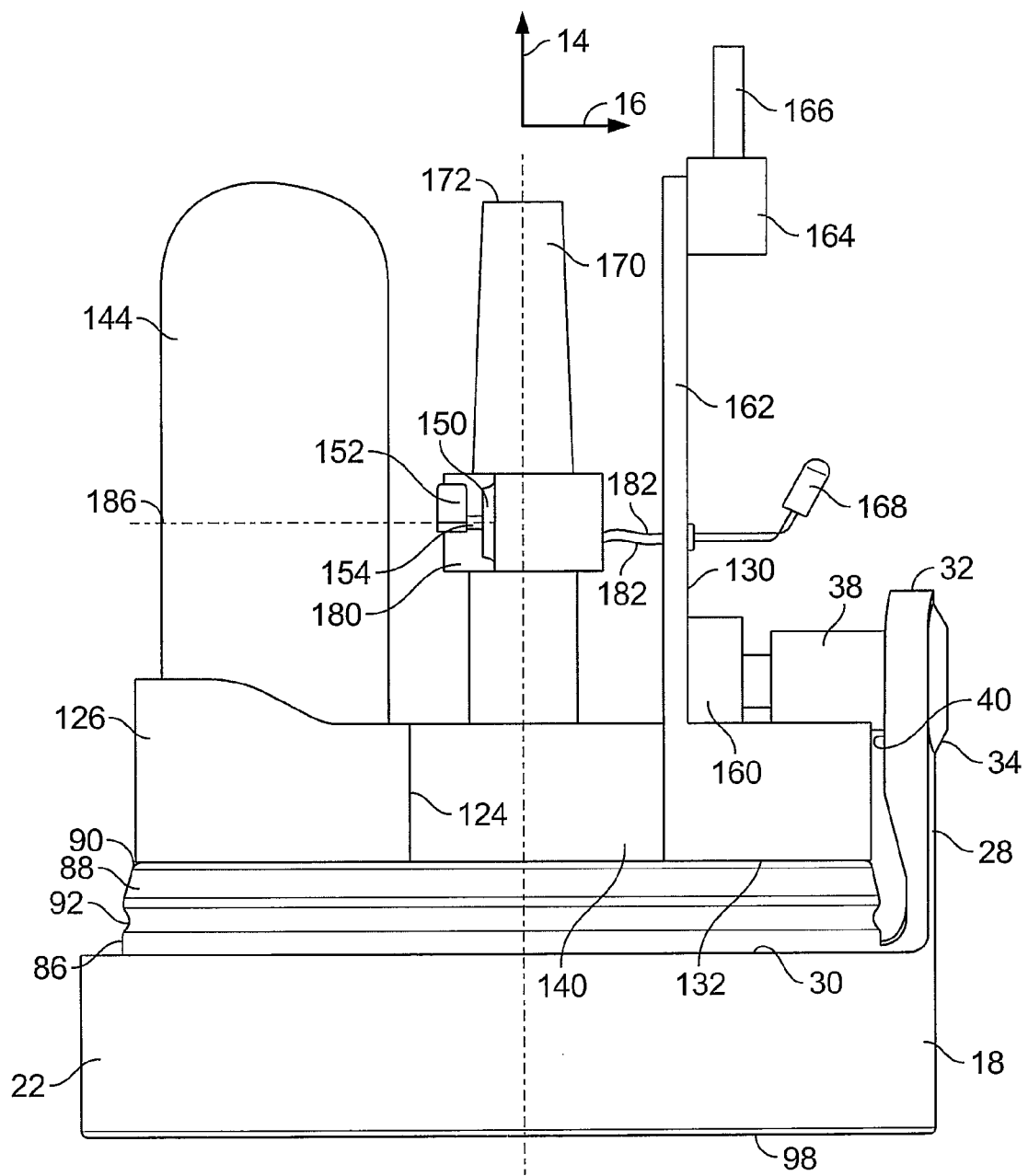
FIG. 12C is a is a left side elevational view of the overcap of FIG. 10 illustrating a third orientation of a vibe motor.

However, the vibe motor 150 may be mounted to the dispensing member 170 with the axis of rotation 186 of the shaft 154 having any orientation. For example, the vibe motor 150 may also be mounted to the dispensing member 170 such that the axis of rotation 186 of the shaft 154 is on about a forty-five degree angle with respect to the longitudinal axis 14, as shown in FIG. 12B. The vibe motor 150 may also be mounted to the dispensing member 170 such that the axis of rotation 186 of the shaft 154 is about substantially perpendicular to the longitudinal axis 14, as shown in FIG. 12C. Indeed, the vibe motor 150 may be mounted to the dispensing member 170 such that the axis of rotation 186 of the shaft 154 has any angle with respect to the longitudinal axis 14.

Further, the vibe motor 150 may be mounted to the dispensing member 170 such that the axis of rotation 186 of the shaft 154 lies in a common plane with the longitudinal axis 14, but is not parallel thereto. For example, the vibe motor 150 may be mounted to the dispensing member 170 such that the axis of rotation 186 of the shaft 154 and the longitudinal axis 14 lie in a common plane with about a forty-five degree angle therebetween, as shown by a first position 188 depicted in dashed lines in FIG. 16B. The vibe motor 150 may also be mounted to the dispensing member 170 such that the axis of rotation 186 of the shaft 154 and the longitudinal axis 14 lie in a common plane with about a ninety degree angle therebetween, as shown by a second position 190 depicted in dashed lines in FIG. 16B.

In addition, it is contemplated that the vibe motor 150 may also be mounted to the dispensing member 170 such that an angle measured between the axis of rotation 186 of the shaft 154 and the longitudinal axis 14 is any angle between zero and ninety degrees, e.g., fifteen degrees, thirty degrees, sixty degrees, seventy-five degrees, etc. In fact, the vibe motor 150 may be mounted to the dispensing member 170 in any other relative orientation or combination of orientations between the longitudinal axis 14 and the axis of rotation 186 that is found to be advantageous to imparting a radial oscillatory displacement to the dispensing member 170.

The dispensing member 170 experiences radial oscillatory displacements in response to the force generated by the vibe motor 150 when activated, and the valve stem 118 activates with each radial oscillatory displacement. The frequency of displacement of the dispensing member 170 depends upon a number of factors including, for example, the offset distance 184 of the vibe motor 150, the mounting distance 185 of the vibe motor 150, the orientation of the vibe motor 150, the force generated by the vibe motor 150, and the physical characteristics of the dispensing member 170 and the valve stem 118. At the rate of rotation of 7000 rpm of the representative vibe motor discussed above, the oscillatory displacements are relatively rapid and are perceived by a person as a continuous spraying. It is contemplated that a dispensing rate of the valve stem 118 could be altered by changing one or more of the factors listed above. For example, during manufacture the vibe motor 150 may be disposed at a greater or lesser distance 184 from the valve stem 118, mounted closer to the discharge end 172 or the bottom end 174 of the dispensing member 170, or replaced by another vibe motor that generates additional force. Further, different materials having more or less elasticity may be used to give the dispensing member 170 and/or the valve stem 118 an enhanced dynamic response. As another example, the vibe motor 150 may be driven at each of several voltage levels in a range just below and above the rated voltage. Each of the several voltage levels causes the vibe motor 150 to generate a different level of force, which in turn corresponds to a different dispensing rate for the valve stem 118. A switch mechanism, in addition to or as part of the switch assembly 164, may be added to the overcap 10 to allow a user to select a voltage level and therefore the dispensing rate of the valve stem 118.

It is also contemplated that the actuation mechanism used to apply oscillatory motion to the valve stem 118 may be a mechanism other than the vibe motor 150. One example of an actuation mechanism is a rotating cam in contact with a lateral surface of the dispensing member 170, wherein the cam is driven by a small motor via a drive transmission. The drive transmission provides precise control of the cam rotation, allowing the cam to be repeatedly rotated at a high rate to create an oscillatory displacement of the dispensing member, or rotated as little as a fraction of a turn to precisely displace the dispensing member. Another example of an actuation mechanism is an electromagnet disposed proximate to a magnetic dispensing member. Each activation of the electromagnet generates a magnetic field that interacts with the magnetic dispensing member to cause radial displacement of same. The amount of force generated by each activation and the frequency of activation of the electromagnet may be conveniently and easily controlled through simple circuitry and a variable control device as known to those of skill in the art. Yet another example of an actuation mechanism is an electronic oscillator circuit that generates high frequency sounds. An electronic oscillator circuit may be placed in an overcap so as to direct sounds therefrom to a surface of the dispensing member 170. The dispensing member 170 may be made of a material that exhibits a dynamic response to the sound, i.e., the material exhibits vibrations when exposed to a standing wave pattern. Still other actuation mechanisms are possible and may be useful herein to activate the tilt-activated valve stem 118, e.g., any of the actuation mechanisms described in U.S. patent application Ser. No. 11/801,557, filed on May 10, 2007, which is herein incorporated by reference in its entirety, may be modified to provide oscillatory motion to the valve stem 118.

Preferably, the dispensing member 170 is repeatedly radially displaced to a discharge position over a predetermined length of time, or spraying period, that includes the radial oscillatory displacement of the valve stem 118. The duration of the spraying period is typically equal to about 170 milliseconds. Indeed, if desired, the dispensing member 170 could be repeatedly radially displaced to the discharge position until all of the container contents are exhausted. Further, the dispensing member 170 may be repeatedly radially displaced over a plurality of spraying periods in response to the occurrence of a single activation signal, wherein the spraying periods are separated by rest periods. Multiple spraying periods may be beneficial when a single extended spraying period from a container is undesirable or when intermittent discharge is desired.

As described above, the valve stem 118 activates with each radial oscillatory displacement. One complete cycle of oscillation encompasses movement of the discharge end 172 of the dispensing member 170 (and the valve stem 118) in a first radial direction to a first maximum deflection, followed by motion in a second radial direction to a second maximum deflection, which may or may not be diametrically opposed to the first radial direction. A first oscillation cycle may be followed by one or more subsequent oscillation cycles prior to the valve stem 118 and the dispensing member 170 returning to a non-actuation position. Every complete cycle of oscillatory displacement of the discharge end 172 of the dispensing member 170 therefore has two points of maximum radial displacement. Any point along a cycle of oscillatory displacement of the discharge end 172 where the valve stem 118 is discharging product may be considered an actuation position. Assuming that the dispensing member 170 attains a frequency of oscillation roughly equivalent to the rotation rate of the representative vibe motor presented above, the dispensing member 170 attains a frequency of oscillation of about 7,000 Hz. In one embodiment, a range of frequencies of oscillation attainable by the dispensing member 170 is about 1,000 Hz to about 10,000 Hz. Therefore the period of a cycle of oscillation of the dispensing member varies between about 1 millisecond and about 0.1 millisecond.

Figure 17:
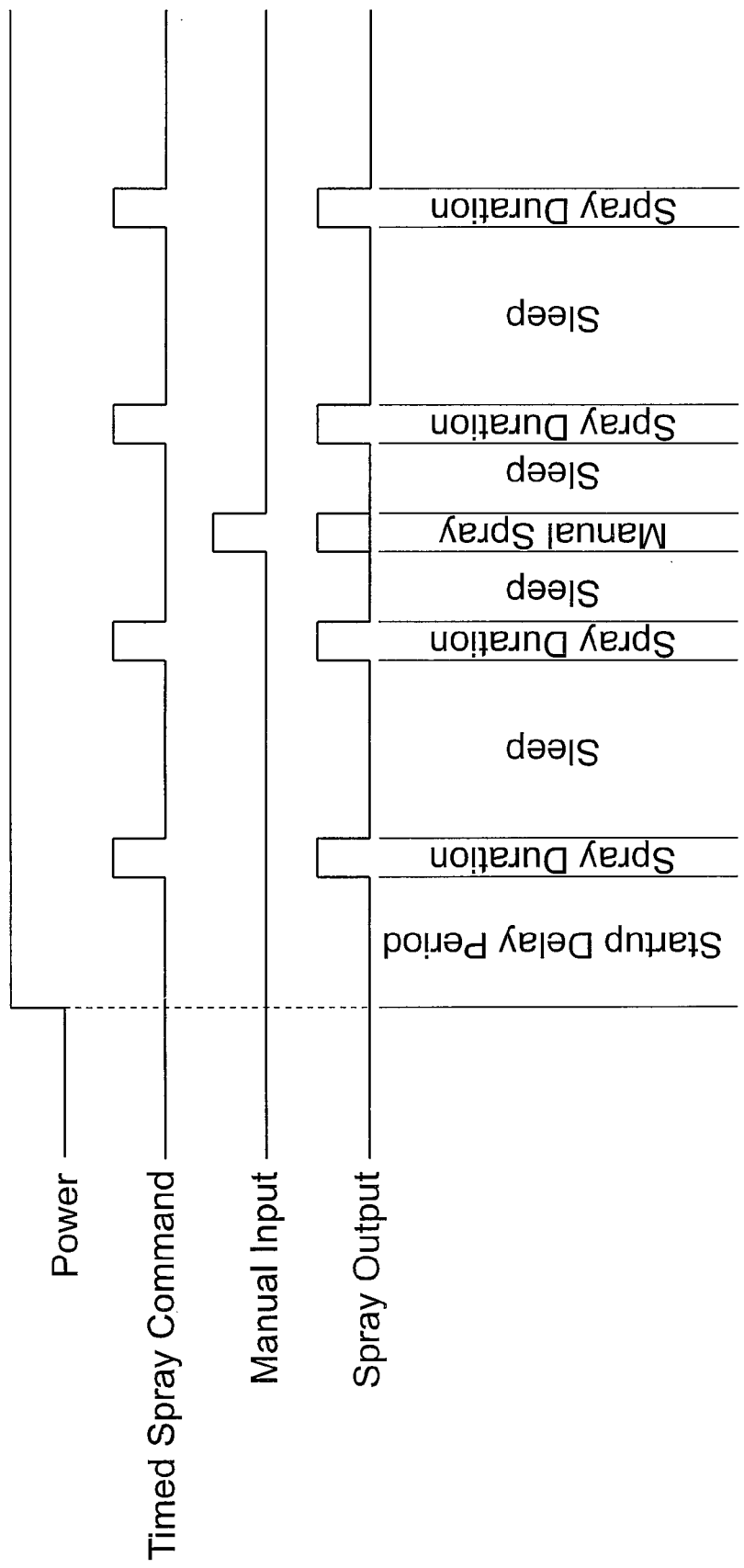
FIG. 17 is a timing diagram illustrating the operation of the overcap of FIGS. 1-16B according to a first operational sequence.

FIG. 17 depicts a timing diagram that illustrates the operation of the overcap 10 during an in use condition. Initially, the overcap 10 is energized by moving the finger 166 of the switch assembly 164 from an "OFF" position to one of four operating modes 192, 194, 196, 198, whereupon a control circuit (not shown), which may be etched on the printed circuit board 162, causes the overcap 10 to enter a startup delay period. Each of the four operating modes 192, 194, 196, 198 corresponds to a predetermined sleep period between consecutive spraying periods. For example, the first operating mode 192 may correspond to a five minute sleep period, the second operating mode 194 may correspond to a seven and a half minute sleep period, the third operating mode 196 may correspond to a fifteen minute sleep period, and the fourth operating mode 198 may correspond to a thirty minute sleep period. For the present example, we shall assume the first operating mode 192 has been chosen. Upon completion of the startup delay period, the vibe motor 150 is activated to discharge fluid from the overcap 10 during a first spraying period. The startup delay period is preferably about three seconds long, and the spraying period is typically about 170 milliseconds long. Upon completion of the first spraying period, the overcap 10 enters a first sleep period that lasts 5 minutes. Upon expiration of the first sleep period the vibe motor 150 is activated to discharge fluid during a second spraying period. Thereafter, the overcap 10 enters a second sleep period that lasts for 5 minutes. In the present example, the second sleep period is interrupted by the manual activation of the overcap 10, whereupon fluid is dispensed during a third spraying period. Automatic operation thereafter continues with alternating sleep and spraying periods. At any time during a sleep period, the user may manually activate the overcap 10 for a selectable or fixed period of time by depressing the pushbutton 34. Upon termination of the manual spraying operation, the overcap 10 completes the pending sleep period. Thereafter, a spraying operation is undertaken.

In another embodiment, the switch assembly 164 may have a continuous range of settings instead of the four distinct operating modes 192, 194, 196, 198 described above. In such an embodiment, the switch assembly 164 may be provided with a switch mechanism such as a dial (not shown), that provides for continuous user variation of the spraying period and/or the sleep period between continuous spray and periods lasting several hours or days. In a further embodiment, the switch assembly 164 may be replaced and/or supplemented by a photocell light sensor, which may be used as a motion detector. Other motion detectors known to those of skill in the art may also be utilized e.g., a passive infrared or pyro-electric motion sensor, an infrared reflective motion sensor, an ultrasonic motion sensor, or a radar or microwave radio motion sensor. The photocell collects ambient light and allows the control circuit to detect any changes in the intensity thereof. Filtering of the photocell output is undertaken by the control circuit. If the control circuit determines that a threshold light condition has been reached, e.g., a predetermined level of change in light intensity, the control circuit develops a signal to activate the vibe motor 150. For example, if the overcap 10 is placed in a lit bathroom, a person walking past the sensor may block a sufficient amount of ambient light from reaching the sensor to cause the control circuit to activate the vibe motor 150 and discharge a fluid.

It is also envisioned that the switch assembly 164 may be replaced or supplemented with a vibration sensor, an odor sensor, a heat sensor, or any other sensor known to those skilled in the art. Alternatively, more than one sensor may be provided in the overcap in lieu of the switch assembly 164 or in combination with same. It is anticipated that one skilled in the art may provide any type of sensor either alone or in combination with the switch assembly 164 and/or other sensors to meet the needs of a user. In one particular embodiment, the switch assembly 164 and a sensor are provided in the same overcap. In such an embodiment, a user may choose to use the timer-based switch assembly 164 to automatically operate the vibe motor 150 of the overcap 10, or the user may choose to use the sensor to detect a given event prior to activating the overcap 10. Alternatively, the overcap 10 may operate in a timer and sensor based mode of operation concurrently.

The LED 168 illuminates the light transmissive rod 78 when the overcap 10 is in an operative state. The LED 168 blinks intermittently once every fifteen seconds during the sleep period. Depending on the selected operating mode, the blinking frequency of the LED 168 begins to increase as a spraying period becomes imminent. The more frequent illumination of the LED 168 serves as a visual indication that the overcap 10 is about to discharge fluid contents into the atmosphere.

Figure 18:
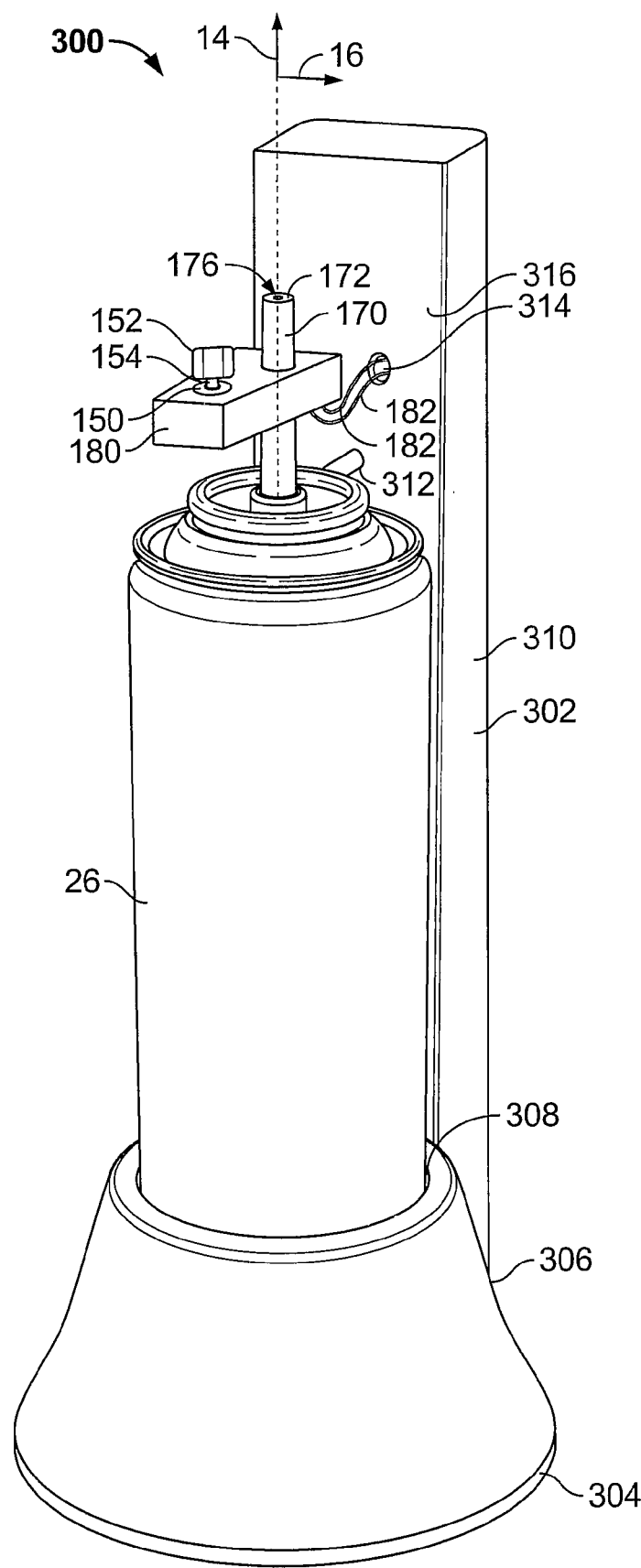
FIG. 18 is an isometric view of another embodiment of a device showing a frame, a fluid container, and a vibe motor.

In another embodiment depicted in FIG. 18, the aerosol container 26 is placed within a device 300 having a frame 302. The frame 302 includes a base portion 304 and a tapered cylindrical wall 306. A recess 308 is provided within the base portion 304, which is adapted to receive the aerosol container 26 therein. A column 310 is integral with and extends upwardly from the base portion 304. The column 310 extends beyond a greatest longitudinal extent of the aerosol container 26. A finger 312 extends from the column 310 to space the aerosol container 26 from the column 310. The vibe motor 150 is attached to the dispensing member 170 by the coupling member 180. The wires 182 extend through an aperture 314 in a front wall 316 of the column 310. Electronics such as a circuit board (not shown) and a power supply (not shown) are housed within the column 310. During an operational sequence, which may include any of the operational sequences or methodologies described herein, a control circuit (not shown) within the frame 302 generates an electrical signal in response to an elapsed timer, sensor input, or manual activation. The signal energizes the vibe motor 150, which causes radial oscillatory forces to act upon the dispensing member 170. As discussed above, the application of sufficient radial forces to the dispensing member 170 causes radial displacement of the valve stem 118. In other embodiments, the frame 302 may be part of a larger housing (not shown) that completely encapsulates the aerosol container 26. Such a housing includes a discharge orifice generally aligned with the discharge end 172 of the dispensing member 170. The housing may be free-standing for installation on a horizontal surface such as a floor or a shelf, or may be mounted to a vertical surface such as a wall or support column.

Any of the embodiments described herein may be modified to include any of the structures or methodologies disclosed in connection with different embodiments. Further, the present disclosure is not limited to aerosol containers of the type specifically shown. Still further, the overcaps of any of the embodiments disclosed herein may be modified to work with any type of fluid container having a tilt-activated valve stem.

INDUSTRIAL APPLICABILITY

Aerosol dispensers are commonly used to dispense volatile materials such as air fresheners, deodorants, insecticides, germicides, decongestants, perfumes, and the like, that are stored within aerosol containers. Automated valve activation systems for aerosol containers allow the contents thereof to be released without human interaction, for example, according to a predetermined time schedule. Tilt-activated valve stems for aerosol container release valves typically require less force to operate than vertically activated valve stems. A system for automatically activating a tilt-activated valve stem by a vibe motor is presented. The system may be installed in a typical overcap for use with ordinary tilt-activated aerosol containers, resulting in an improvement in utility of the aerosol container.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

A dispensing system includes a tilt-activated valve stem operably connected to a valve on a container. The tilt-activated valve stem is disposed in a non-actuation position during a non-activation state and is moved between a first actuation position and a second actuation position during an activation state. The first actuation position is offset radially from the non-actuation position in a first actuation direction and the second actuation position is offset radially from the non-actuation position in a second actuation direction.

We claim:
1. An overcap for a volatile material container, comprising:
   a housing mounted on a container having a tilt-activated valve stem operably connected to a valve; and
   a vibe motor disposed within the housing, wherein the vibe motor includes a shaft and a head eccentrically mounted to the shaft, wherein eccentric rotation of the head results in a dynamic imbalance of the vibe motor, and wherein the dynamic imbalance causes the vibe motor to impart radial displacement to the valve stem.

2. The overcap of claim 1, wherein the housing includes a power source for providing power to the vibe motor.

3. The overcap of claim 1, wherein the housing includes an electrical lead adapted to be plugged into an A.C. outlet.

4. The overcap of claim 1, wherein the housing includes a switch assembly for adjusting a timer interval between the intermittent activation of the vibe motor by a control circuit.

5. The overcap of claim 1, wherein the housing includes a manual actuation button for generating a signal to cause a control circuit to activate the vibe motor.

6. The overcap of claim 1, wherein the housing is mounted on a container having a tilt-activated valve stem operably connected to a valve.

7. An overcap for a volatile material container, comprising:
a housing mounted on a container having a tilt-activated valve stem operably connected to a valve; and
a vibe motor disposed within the housing, wherein the vibe motor includes a shaft and a head eccentrically mounted to the shaft, wherein eccentric rotation of the head results in a dynamic imbalance of the vibe motor, and wherein the dynamic imbalance causes the vibe motor to impart radial displacement to the valve stem upon activation in response to a signal from at least one of a timer, a sensor, or a manual activator.

8. The overcap of claim 7, wherein the sensor is a photocell light sensor.

9. The overcap of claim 7, wherein a switch assembly is provided to allow for user-selected adjustment of operating intervals of a timer.

10. The overcap of claim 9, wherein the switch assembly is adapted to provide a continuously variable adjustment of operating intervals.

11. The overcap of claim 9, wherein the housing is mounted on a container having a tilt-activated valve stem operably connected to a valve.

12. A dispensing system, comprising:
a tilt-activated valve stem operably connected to a valve on a container, wherein the tilt-activated valve stem is disposed in a non-actuation position during a non-activation state, and wherein the tilt-activated valve stem is moved between a first actuation position and a second actuation position during an activation state,
wherein the first actuation position is offset radially from the non-actuation position in a first actuation direction, wherein the second actuation position is offset radially from the non-actuation position in a second actuation direction, and wherein a vibe motor moves the tilt-activated valve stem between the first actuation position and the second actuation position.

* * * * *